United States Patent
Madiyalakan et al.

(10) Patent No.: US 11,773,183 B2
(45) Date of Patent: Oct. 3, 2023

(54) MUC16 MONOCLONAL ANTIBODY AND USES THEREOF

(71) Applicant: QUEST PHARMATECH INC., Edmonton (CA)

(72) Inventors: Ragupathy Madiyalakan, Edmonton (CA); Michael Hollingsworth, Ohama, NE (US); Prakash Radhakrishnan, Ohama, NE (US)

(73) Assignee: QUEST PHARMATECH INC., Edmonton (CA)

( * ) Notice: Subject to any disclaimer, the term of this patent is extended or adjusted under 35 U.S.C. 154(b) by 320 days.

(21) Appl. No.: 17/048,119

(22) PCT Filed: Apr. 30, 2019

(86) PCT No.: PCT/CA2019/050565
§ 371 (c)(1),
(2) Date: Oct. 16, 2020

(87) PCT Pub. No.: WO2019/213747
PCT Pub. Date: Nov. 14, 2019

(65) Prior Publication Data
US 2021/0101994 A1     Apr. 8, 2021

Related U.S. Application Data

(60) Provisional application No. 62/669,058, filed on May 9, 2018.

(51) Int. Cl.
*C07K 16/30* (2006.01)
*A61K 45/06* (2006.01)

(52) U.S. Cl.
CPC .......... *C07K 16/3092* (2013.01); *A61K 45/06* (2013.01); *C07K 2317/24* (2013.01);
(Continued)

(58) Field of Classification Search
CPC ............ C07K 16/3092; C07K 2317/24; C07K 2317/565; C07K 2317/567;
(Continued)

(56) References Cited

FOREIGN PATENT DOCUMENTS

WO    WO2016149368    9/2016

OTHER PUBLICATIONS

Lutz Riechmann, Serge Muyldermans, Single domain antibodies: comparison of camel VH and camelised human VH domains, Journal of Immunological Methods, vol. 231, Issues 1-2, 1999, pp. 25-38. (Year: 1999).*

(Continued)

*Primary Examiner* — Joanne Hama
*Assistant Examiner* — Adam Yamasaki Ring
(74) *Attorney, Agent, or Firm* — McDonnell Boehnen Hulbert & Berghoff LLP

(57) ABSTRACT

The present document describes an antibody or an antigen-binding fragment that bind to O-glycan mucin-type glycoprotein MUC16 comprising three variable heavy domain complementarity determining regions (CDR)(CDR H1, H2 and H3), and three variable lighy domain CDR (CDR L1, L2 and L3). The present invention also relates to pharmaceutical compositions, nucleic acid vectors, cells comprising the nucleic acid vectors, and methods of inhibiting tumor growth of a tumor expressing O-glycan mucin-type glycoprotein MUC16.

18 Claims, 12 Drawing Sheets

Specification includes a Sequence Listing.

(52) U.S. Cl.
CPC .. *C07K 2317/565* (2013.01); *C07K 2317/567* (2013.01); *C07K 2317/569* (2013.01); *C07K 2317/622* (2013.01)

(58) Field of Classification Search
CPC ........ C07K 2317/569; C07K 2317/622; C07K 2317/73; A61K 45/06; A61K 31/337; A61K 31/517; A61K 31/7068; A61K 39/39558; A61K 39/395; G01N 2400/02; G01N 33/57438; A61P 35/00
See application file for complete search history.

(56) References Cited

OTHER PUBLICATIONS

Rossotti, M.A., Bélanger, K., Henry, K.A. and Tanha, J. (2022), Immunogenicity and humanization of single-domain antibodies. FEBS J, 289: 4304-4327. https://doi.org/10.1111/febs.15809 (Year: 2022).*

Fernández-Quintero, et al., Germline-Dependent Antibody Paratope States and Pairing Specific VH-VL Interface Dynamics, Frontiers in Immunology, vol. 12 (Year: 2021).*

Maeda, et al., "Solution Structure of the SEA Domain from the Murine Homologue of Ovarian Cancer Antigen CA125 (MUC16)", The Journal of Biological Chemistry, 279:13174-13182 (2004).

Gipson, et al., "Generation and characterization of a monoclonal antibody to the cytoplasmic tail of MUC16", Glycobiology, 27:920-926 (2017).

Rao, et al., "Antibodies Against Specific MUC16 Glycosylation Sites Inhibit Ovarian Cancer Growth", ACS Chem Biol, 12:085-2096 (2017).

International Search Report for International Application No. PCT/CA2019/050565 dated Jul. 5, 2019.

Written Opinion for International Application No. PCT/CA2019/050565 dated Jul. 5, 2019.

* cited by examiner

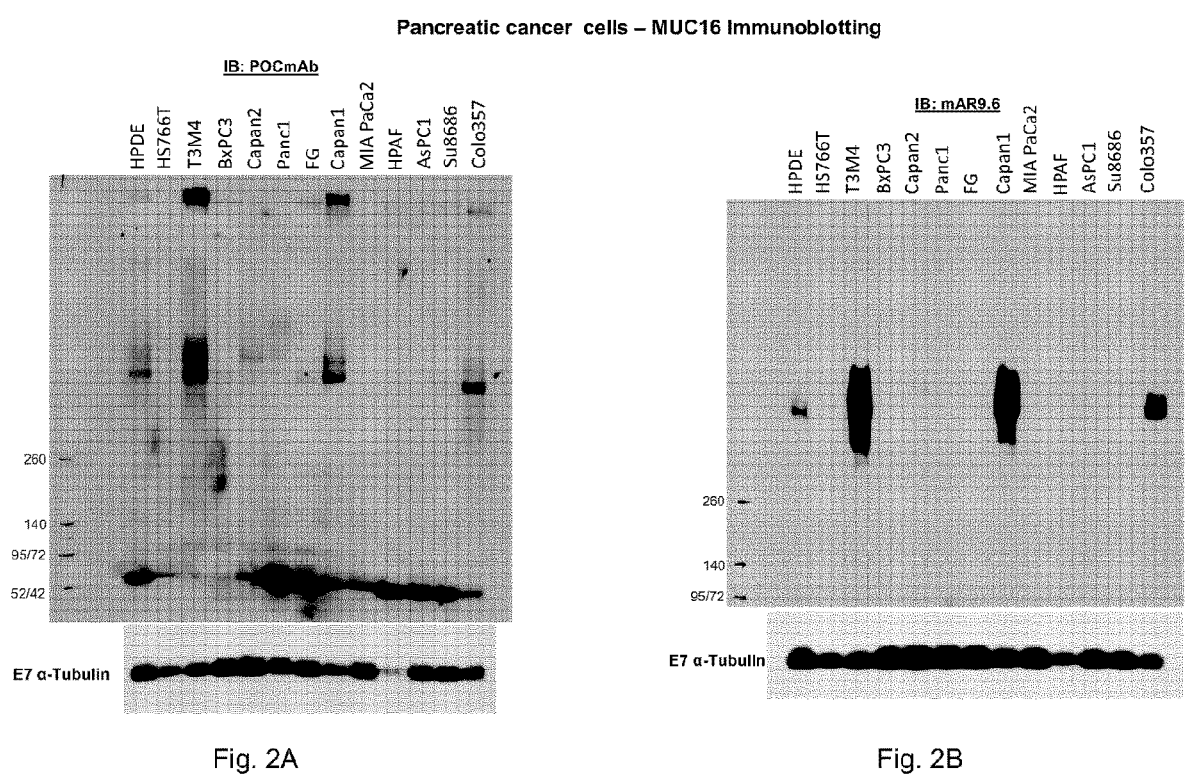
Fig. 2A                    Fig. 2B

Pancreatic cancer ascites fluid – MUC16 Immunoblotting

MUC16 MONOCLONAL ANTIBODY AND USES THEREOF

CROSS-REFERENCE TO RELATED APPLICATIONS

This application is a U.S. National Phase application under 35 U.S.C. § 371 of PCT/CA2019/050565, filed Apr. 30, 2019 which claims priority from and the benefit of U.S. Provisional Application No. 62/669,058, filed on May 9, 2018. The entire disclosure contents of these applications are herewith incorporated by reference in their entirety into the present application.

A computer readable form of the Sequence Listing is filed with this application by electronic submission and is incorporated into this application by reference in its entirety. The Sequence Listing is contained in the file created on Oct. 20, 2020, having the file name "20-1619-US_Sequence-Listing_SEQ_2020-10-20.txt" and is 7.56 kb in size.

BACKGROUND

(a) Field

The subject matter disclosed generally relates to monoclonal antibodies against O-glycan mucin-type glycoproteins. More specifically, the subject matter relates to monoclonal antibodies against O-glycan mucin-type glycoproteins MUC16 and methods of using the same.

(b) Related Prior Art

Pancreatic adenocarcinoma is the fourth-leading cause of cancer-related death in the United States with a 5 year survival rate of less than 4% and a median survival of less than 6 months. According to the American Cancer Society, the estimated number of new cases and deaths due to pancreatic cancer in the US in 2013 are 45,220 and 38,460, respectively. At the time of diagnosis more than 80% of pancreatic cancer patients have either locally advanced or highly metastatic disease.

Currently, Folfirinox is the first line of treatment for patients with metastatic disease and good performance status and gemcitabine alone or in combination with Abraxane is the first-line chemotherapeutic agent for the treatment of other patients with pancreatic adenocarcinoma. However, the response rate is modest, and median overall survival remains dismal. Poor patient response to chemotherapy and poor prognosis are due in part to constitutive activation of oncogenic signaling pathways that are associated with development of drug resistance, aggressive tumorigenicity and early metastasis.

These adverse effects result in a need for a novel molecularly targeted therapy to combat lethal cancers generally including, without limitation, pancreatic cancers.

It is well established that aberrant expression of membrane mucin MUC16 is associated with tumor progression and metastasis of cancers such as ovarian and pancreatic cancer. The role of MUC16 in tumor progression and metastasis occurs through interaction with oncogenic modulators. For instance, it is understood that aberrant expression of MUC16 in ovarian cancer cells facilitates peritoneal metastasis through interactions with mesothelin (tumor differentiation factor) and through immunosuppressive functions by blocking natural killer cell-mediated cytotoxicity, while overexpression of MUC16 increases breast cancer cell proliferation via stimulation of Janus kinase 2 (JAK2). It is also understood that MUC16 is upregulated in pancreatic cancers, and expression is increased in liver metastases—although expression of MUC16 was not detected in pancreatic intraepithelial neoplasia (PanIN) nor in normal pancreas, suggesting that expression of MUC16 may occur later in disease progression.

Despite the role of MUC16 in disease progression being known, little is known about a possible role of oligosaccharide (O-linked glycosylation) modifications on mucin type glycoproteins. Research shows that a higher percentage of truncated O-glycan (Tn and sialyl Tn, STn) expression occurs in pancreatic adenocarcinoma, relative to other types of carcinomas, and it is well established that aberrant expression of truncated O-glycans is associated with tumour progression and adverse patient outcome. For example, STn antigen is expressed by more than 80% of human carcinomas, and in all cases the detection of STn correlates with poor prognosis and decreased overall survival of patients. Further, expression of tumour associated truncated carbohydrate antigens Tn and STn on mucin type glycoproteins are among the most common tumour-specific oligosaccharide alterations observed in adenocarcinomas. Appearance of Tn and STn epitopes on cancer cell surfaces are due to overexpression of ST6GalNAc-1 or lack of core 3 synthase/core 1 synthase activity and/or defects in Core 1 synthase specific molecular chaperone—Cosmc. Overexpression of STn antigen has been observed on many epithelial cancer cells, but the highest frequency is observed in pancreatic cancer. For example, overexpression of STn occurs early on in tumor progression on epithelial cancer cells (e.g. early epithelial benign lesions) and pancreatic cancer (e.g. pancreatic intraepithelial neoplasia stage III (PanIN-3)), which is a premalignant lesion thought to precede development of pancreatic adenocarcinoma. Altogether, these findings indicate that overexpression of truncated O-glycans is an early event leading to pancreatic cancer development. However, the exact biological mechanism of these truncated O-glycans during pancreatic tumorigenesis may not be well understood.

Notwithstanding over two decades of research, attempts to utilize known biomarkers of cancer, such as mucin-type O-glycan MUC16, in the development of molecularly targeted therapies for cancer have failed.

Therefore, there is a need for novel method for use of monoclonal antibodies that target O-glycans on mucin-type glycoproteins to inhibit activation of pro-survival cell signaling pathways.

Therefore, there is a need for alternative molecularly targeted therapies for targeting O-glycan mucin-type glycoprotein MUC16.

SUMMARY

According to an embodiment, there is provided an antibody or an antigen-binding fragment thereof that binds to O-glycan mucin-type glycoprotein MUC16 comprising three variable heavy domain complementarity determining regions (CDR)(CDR H1, H2 and H3), and three variable light domain CDR (CDR L1, L2 and L3), wherein the CDR H1, H2, H3, L1, L2, and L3 comprise an amino acid sequence comprising:

CDR H1:

(SEQ ID NO: 1)

GFTFSTF,

```
CDR H2:
                                   (SEQ ID NO: 2)
SSGSST,

CDR H3:
                                   (SEQ ID NO: 3)
SGYDYDPIYYALDY,

CDR L1:
                                   (SEQ ID NO: 4)
RASESVDNYGISFMN,

CDR L2:
                                   (SEQ ID NO: 5)
GASNQGS,
and

CDR L3:
                                   (SEQ ID NO: 6)
QQTKEVPWT,
``` respectively.

According to another embodiment, there is provided an antibody or an antigen-binding fragment thereof that binds to O-glycan mucin-type glycoprotein MUC16 comprising three variable heavy domain complementarity determining regions (CDR)(CDR H1, H2 and H3), wherein the CDR H1, H2 and H3 comprise an amino acid sequence comprising:

```
CDR H1:
                                   (SEQ ID NO: 1)
GFTFSTF,

CDR H2:
                                   (SEQ ID NO: 2)
SSGSST,
and

CDR H3:
                                   (SEQ ID NO: 3)
SGYDYDPIYYALDY,
``` respectively.

According to another embodiment, there is provided an antibody or an antigen-binding fragment thereof that binds to O-glycan mucin-type glycoprotein MUC16 comprising three variable light domain complementarity determining regions (CDR)(CDR L1, L2 and L3), wherein the CDR L1, L2, and L3 comprise an amino acid sequence comprising:

```
CDR L1:
                                   (SEQ ID NO: 4)
RASESVDNYGISFMN,

CDR L2:
                                   (SEQ ID NO: 5)
GASNQGS,
and

CDR L3:
                                   (SEQ ID NO: 6)
QQTKEVPWT,
``` respectively.

The antibody or antigen binding fragment of the present invention may further comprise four variable heavy domain framework regions (HFR)(HFR 1, 2, 3 and 4), wherein the HFR 1, 2, 3, and 4 comprise an amino acid sequence comprising:

```
HFR 1:
                                   (SEQ ID NO: 7)
EVQLVESGGGLVQPGGSRKLSCAAS,

HFR 2:
                                   (SEQ ID NO: 8)
GMHWVRQAPEKGLEWVAYI,

HFR 3:
                                   (SEQ ID NO: 9)
IYYGDTLQGRFIISRDNPKNTLFLQMTSLRSEDTAMYYCAR,
and

HFR 4:
                                   (SEQ ID NO: 10)
WGQGTSVTVSS.
```

The antibody or antigen binding fragment thereof of the present invention may further comprise four variable light domain framework regions (LFR)(LFR 1, 2, 3 and 4), wherein the LFR 1, 2, 3, and 4 comprise an amino acid sequence comprising:

```
LFR 1:
                                   (SEQ ID NO: 11)
DIVLTQSPASLAVSLGQRATISC,

LFR 2:
                                   (SEQ ID NO: 12)
WFQQKPGHPPKLLIY,

LFR 3:
                                   (SEQ ID NO: 13)
GVPARFSGSGSGTDFSLNIHPMEEDDAAMYFC,
and

LFR 4:
                                   (SEQ ID NO: 14)
FGGGTKVEIKR.
```

The antibody or antigen binding fragment thereof of the present invention may further comprise a variable heavy domain ($V_H$) comprising amino acid sequence comprising:

```
                                   (SEQ ID NO: 15)
EVQLVESGGGLVQPGGSRKLSCAASGFTFSTFGMHVVVRQAPEKGL

EWVAYISSGSSTIYYGDTLQGRFIISRDNPKNTLFLQMTSLRSEDT

AMYYCARSGYDYDPIYYALDYWGQGTSVTVSS.
```

The antibody or antigen binding fragment thereof of the present invention may further comprise a variable light domain ($V_L$) comprising amino acid sequence comprising:

```
                                   (SEQ ID NO: 16)
DIVLTQSPASLAVSLGQRATISCRASESVDNYGISFMNWFQQKPGH

PPKLLIYGASNQGSGVPARFSGSGSGTDFSLNIHPMEEDDAAMYFC

QQTKEVPWTFGGGTKVEIKR.
```

The antibody or antigen binding fragment thereof of the present invention may further comprise a variable heavy domain ($V_H$) comprising amino acid sequence comprising:

```
                                   (SEQ ID NO: 15)
EVQLVESGGGLVQPGGSRKLSCAASGFTFSTFGMHWVRQAPEKGLE

WVAYISSGSSTIYYGDTLQGRFIISRDNPKNTLFLQMTSLRSEDTA

MYYCARSGYDYDPIYYALDYWGQGTSVTVSS,
``` and a variable light domain ($V_L$) comprising amino acid sequence comprising:

(SEQ ID NO: 16)
DIVLTQSPASLAVSLGQRATISCRASESVDNYGISFMNWFQQKPGHP

PKLLIYGASNQGSGVPARFSGSGSGTDFSLNIHPMEEDDAAMYFCQ

QTKEVPWTFGGGTKVEIKR.

The antibody or antigen-binding fragment thereof may be an IgA, IgD, IgE, IgG, or IgM.

The antigen-binding fragment may be a single-domain antibody (sdAb), or a single-chain variable fragment (scFv).

The sdAb may comprise three CDR (CDR1, 2 and 3) comprising SEQ ID NO:1, SEQ ID NO:2, and SEQ ID NO:3, respectively.

The sdAb may comprise three CDR (CDR1, 2 and 3) comprising SEQ ID NO:4, SEQ ID NO:5, and SEQ ID NO:6, respectively.

The antibody or an antigen-binding fragment thereof may be humanized or partially humanized.

The antibody or antigen binding fragment thereof may be POCmAb.

According to another embodiment, there is provided a composition comprising the antibody or antigen-binding fragment thereof of the present invention, and a pharmaceutically acceptable diluent, carrier or excipient.

According to another embodiment, there is provided a method of inhibiting tumor growth of a tumor expressing O-glycan mucin-type glycoprotein MUC16 in a subject in need thereof, comprising administering to the subject an antibody or an antigen binding fragment thereof that targets O-glycan mucin-type glycoprotein MUC16, according to the present invention, or a composition according to the present invention.

The antibody or an antigen binding fragment thereof may be an antibody.

The antibody may be a monoclonal antibody.

The O-glycan mucin-type glycoprotein MUC16 may comprise a truncated O-glycan.

The truncated O-glycan may comprise a Tn antigen, a sialyl Tn antigen (STn), or a combination thereof.

The method may further comprise administering a second therapeutic agent comprising at least one of a cytotoxic agent, an additional antibody or a therapeutically active fragment thereof, or a chemotherapy regimen.

The cytotoxic agent may be at least one of an inhibitor of ErbB signaling, an inhibitor of phosphoinositide 3-kinases (PI3Ks) Akt signaling, or combinations thereof.

The cytotoxic agent may be at least one of gemcitabine and abraxane.

The inhibitor of ErbB signaling may be Sapitinib.

The additional antibody or therapeutically fragment thereof may be oregovomab antibody B43.13, AR9.6 antibody, or combinations thereof.

The chemotherapy regimen may be Folfirinox.

The tumor may be chosen from a pancreatic tumor, a gall bladder tumor, a gastric tumor, a colon tumor, an ovarian tumor, a breast tumor, and a liver tumor.

The method may be for the treatment of a cancer.

The antibody or an antigen binding fragment thereof may bind to a conformational epitope of tandem repeat (TR) SEA domain 5 and 6 without glycosylation of the O-glycan mucin-type glycoprotein MUC16.

According to another embodiment, there is provided a method of detection of a tumor expressing O-glycan mucin-type glycoprotein MUC16 in a subject in need thereof, comprising administering to the subject an antibody or an antigen binding fragment thereof specific to O-glycan mucin-type glycoprotein MUC16 according to the present invention and detecting the antibody or antigen binding fragment.

The antibody or antigen binding fragment may thereof further comprise a detectable label.

The detectable label may be a fluorescent marker, a radioactive marker, an MRI contrast agent, or combinations thereof.

According to another embodiment, there is provided a nucleic acid vector comprising a nucleotide sequence encoding an antibody or an antigen-binding fragment thereof of the present invention.

According to another embodiment, there is provided a cell comprising the nucleic acid vector of the present invention for expressing the antibody or antigen-binding fragment thereof of the present invention.

According to another embodiment, there is provided the use of an antibody or an antigen binding fragment thereof that targets O-glycan mucin-type glycoprotein MUC16, according to the present invention, or of a composition according to the present invention, for inhibiting tumor growth of a tumor expressing O-glycan mucin-type glycoprotein MUC16 in a subject in need thereof.

The antibody or an antigen binding fragment thereof may be an antibody.

The antibody may be a monoclonal antibody.

The O-glycan mucin-type glycoprotein MUC16 may comprise a truncated O-glycan.

The truncated O-glycan may comprise a Tn antigen, a sialyl Tn antigen (STn), or a combination thereof.

The use may further comprise administering a second therapeutic agent comprising at least one of a cytotoxic agent, an additional antibody or a therapeutically active fragment thereof, or a chemotherapy regimen.

The cytotoxic agent may be at least one of an inhibitor of ErbB signaling, an inhibitor of phosphoinositide 3-kinases (PI3Ks)/Akt signaling, or combinations thereof.

The cytotoxic agent may be at least one of gemcitabine and abraxane.

The inhibitor of ErbB signaling may be Sapitinib.

The additional antibody or therapeutically fragment thereof may be oregovomab antibody B43.13, AR9.6 antibody, or combinations thereof.

The chemotherapy regimen may be Folfirinox.

The tumor may be chosen from a pancreatic tumor, a gall bladder tumor, a gastric tumor, a colon tumor, an ovarian tumor, a breast tumor, and a liver tumor.

The use may be for the treatment of a cancer.

The antibody or an antigen binding fragment thereof may bind to a conformational epitope of tandem repeat (TR) SEA domain 5 and 6 without glycosylation of the O-glycan mucin-type glycoprotein MUC16.

According to another embodiment, there is provided an antibody or an antigen binding fragment thereof that targets O-glycan mucin-type glycoprotein MUC16, according to the present invention for use in inhibiting tumor growth of a tumor expressing O-glycan mucin-type glycoprotein MUC16 in a subject in need thereof.

According to another embodiment, there is provided an antibody or an antigen binding fragment thereof that targets O-glycan mucin-type glycoprotein MUC16, according to the present invention for use in a method of inhibiting tumor growth of a tumor expressing O-glycan mucin-type glycoprotein MUC16 in a subject in need thereof.

The antibody or antigen binding fragment for use of the present invention may be an antibody.

The antibody may be a monoclonal antibody.

The O-glycan mucin-type glycoprotein MUC16 may comprise a truncated O-glycan.

The truncated O-glycan may comprise a Tn antigen, a sialyl Tn antigen (STn), or a combination thereof.

The antibody or an antigen binding fragment for use of the present invention, may further comprise administering a second therapeutic agent comprising at least one of a cytotoxic agent, an additional antibody or a therapeutically active fragment thereof, or a chemotherapy regimen.

The cytotoxic agent may be at least one of an inhibitor of ErbB signaling, an inhibitor of phosphoinositide 3-kinases (PI3Ks)/Akt signaling, or combinations thereof.

The cytotoxic agent may be at least one of gemcitabine and abraxane.

The inhibitor of ErbB signaling may be Sapitinib.

The additional antibody or therapeutically fragment thereof may be oregovomab antibody B43.13, AR9.6 antibody, or combinations thereof.

The chemotherapy regimen may be Folfirinox.

The tumor may be chosen from a pancreatic tumor, a gall bladder tumor, a gastric tumor, a colon tumor, an ovarian tumor, a breast tumor, and a liver tumor.

The antibody or an antigen binding fragment for use of the present invention may be for the treatment of a cancer.

The antibody or an antigen binding fragment thereof may bind to a conformational epitope of tandem repeat (TR) SEA domain 5 and 6 without glycosylation of the O-glycan mucin-type glycoprotein MUC16.

The following terms are defined below.

The term "antibody", which is also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme (i.e. CDR1, 2 and 3, for each variable region).

An "antibody fragment", "antigen-binding fragment", and "antigen-binding fragment thereof" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single-domain antibody (sdAb; a fragment composed of a single $V_L$ or $V_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches for their construction.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_H$H. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_H$H, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011a,b; Kim et al, 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The term "scFv" is intended to refer to single-chain variable fragment, although an scFv is not actually a fragment of an antibody, but instead is a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This scFv protein retains the specificity of the original immunoglobulin, despite removal of the constant Fc regions and the introduction of the linker. ScFv molecules were created to facilitate phage display, where it is highly convenient to express the antigen-binding domain as a single peptide. As an alternative, scFv can be created directly from subcloned heavy and light chains derived from a hybridoma.

Divalent (or bivalent) scFvs (di-scFvs, bi-scFvs) can be engineered by linking two scFvs. This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. For example, a diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies have also been produced. They exhibit an even higher affinity to their targets than diabodies.

All of these formats can be composed from variable fragments with specificity for two different antigens, in which case they are types of bispecific antibodies. The furthest developed of these are bispecific tandem di-scFvs, known as bi-specific T-cell engagers (BiTE antibody constructs).

The present invention further encompasses an antibody or an antigen-binding fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to other human antibody fragment framework regions (Fv, scFv, Fab) or to other proteins of similar size and nature onto which CDR can be grafted (Nicaise et al, 2004). In such a case, the conformation of the one or more than one hypervariable loop is likely preserved, and the affinity and specificity of the sdAb for its target (i.e., MUC16) is likely minimally affected. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried nonhumanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would also be amply familiar with methods of preparing such humanized antibody fragments and humanizing amino acid positions.

The antibody or antigen-binding fragment thereof of the present invention may also comprise additional sequences to aid in expression, detection, localization or purification. Any such sequences or tags known to those of skill in the art may be used. For example, and without wishing to be limiting, the antibody or antigen-binding fragment thereof may comprise a targeting or signal sequence [for example, but not limited to an endoplasmic reticulum retention signal (KDEL), a detection/purification tag (for example, but not limited to c-Myc, His5, or His6), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or antigen-binding fragment thereof of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in Zhang et al (2004a; 2004b) and WO2003/046560, where pentabodies are produced by expressing a fusion protein comprising the antibody or fragment thereof of the present invention and the pentamerization domain of the B-subunit of an AB5 toxin family (Merritt & Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule (Zhu et al., 2010). Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Another method known in the art for multimerization is to dimerize the antibody or fragment thereof using an Fc domain, for example, but not limited to human Fc domains. The Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010; Iqbal et al, 2010); the fusion protein is recombinantly expressed then purified. For example, and without wishing to be limiting in any manner, multivalent display formats may encompass chimeric or humanized formats of antibodies $V_H$H linked to an Fc domain, or bi or tri-specific antibody fusions with two or three antibodies $V_H$H recognizing unique epitopes. Such antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al, 2010; Iqbal et al, 2010). The Fc fragment may be fused to the N-terminal or C-terminal end of the V$_H$H or humanized versions of the present invention.

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 1 illustrates O-glycan mucin-type glycoprotein MUC16 and the region of this protein from which the antigen of interest was derived from.

FIG. 2A illustrates the binding specificity of humanized (POCmAb) anti-MUC16 antibody against different pancreatic cancer cells.

FIG. 2B illustrates the binding specificity of murine (mAR9.6) anti-MUC16 antibody against different pancreatic cancer cells.

DETAILED DESCRIPTION

Figure 1:
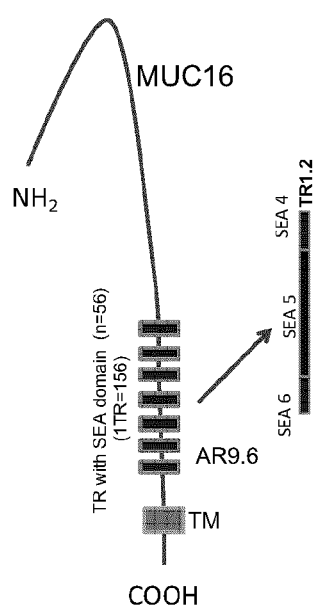

The present invention is directed to alternative antibodies or antigen-binding fragments thereof that bind binds to O-glycan mucin-type glycoprotein MUC16, for use as therapeutics or for diagnostic imaging.

In a first embodiments there is disclosed an antibody or an antigen-binding fragment thereof that binds to O-glycan mucin-type glycoprotein MUC16. The antibody or an antigen-binding fragment thereof comprises three variable heavy domain complementarity determining regions (CDR) (CDR H1, H2 and H3), and three variable light domain CDR (CDR L1, L2 and L3). These CDR H1, H2, H3, L1, L2, and L3 comprise an amino acid sequence comprising CDR H1: GFTFSTF (SEQ ID NO:1), CDR H2: SSGSST (SEQ ID NO:2), CDR H3: SGYDYDPIYYALDY (SEQ ID NO:3), CDR L1: RASESVDNYGISFMN (SEQ ID NO:4), CDR L2: GASNQGS (SEQ ID NO:5), and CDR L3: QQTKEVPWT (SEQ ID NO:6), respectively.

According to a second embodiment, there is disclosed an antibody or an antigen-binding fragment thereof that binds to O-glycan mucin-type glycoprotein MUC16, which comprises three variable heavy domain complementarity determining regions (CDR)(CDR H1, H2 and H3) which comprise an amino acid sequence comprising: CDR H1: GFTFSTF (SEQ ID NO:1), CDR H2: SSGSST (SEQ ID NO:2), and CDR H3: SGYDYDPIYYALDY (SEQ ID NO:3), respectively.

According to a third embodiment, there is disclosed an antibody or an antigen-binding fragment thereof that binds to O-glycan mucin-type glycoprotein MUC16 comprising three variable light domain complementarity determining regions (CDR)(CDR L1, L2 and L3) which comprise an amino acid sequence comprising: CDR L1: RASESVDNYGISFMN (SEQ ID NO:4), CDR L2: GASNQGS (SEQ ID NO:5), and CDR L3: QQTKEVPWT (SEQ ID NO:6), respectively.

In embodiments, the antibody or antigen binding fragment thereof of the present invention may further comprise four variable heavy domain framework regions (HFR)(HFR 1, 2, 3 and 4), which comprise an amino acid sequence comprising:

HFR 1:
(SEQ ID NO: 7)
EVQLVESGGGLVQPGGSRKLSCAAS,

HFR 2:
(SEQ ID NO: 8)
GMHWVRQAPEKGLEWVAYI,

HFR 3:

(SEQ ID NO: 9)
IYYGDTLQGRFIISRDNPKNTLFLQMTSLRSEDTAMYYCAR,
and

HFR 4:

(SEQ ID NO: 10)
WGQGTSVTVSS.

In other embodiments, the antibody or antigen binding fragment thereof of the present invention may further comprise four variable light domain framework regions (LFR) (LFR 1, 2, 3 and 4) which comprise an amino acid sequence comprising:

LFR 1:

(SEQ ID NO: 11)
DIVLTQSPASLAVSLGQRATISC,

LFR 2:

(SEQ ID NO: 12)
WFQQKPGHPPKLLIY,

LFR 3:

(SEQ ID NO: 13)
GVPARFSGSGSGTDFSLNIHPMEEDDAAMYFC,
and

LFR 4:

(SEQ ID NO: 14)
FGGGTKVEIKR.

According to an embodiment, the antibody or antigen binding fragment thereof of the present invention may comprise a variable heavy domain ($V_H$) comprising amino acid sequence comprising:

(SEQ ID NO 15)
EVQLVESGGGLVQPGGSRKLSCAASGFTFSTFGMHWVRQAPEKGLEW

VAYISSGSSTIYYGDTLQGRFIISRDNPKNTLFLQMTSLRSEDTAMY

YCARSGYDYDPIYYALDYWGQGTSVTVSS.

According to an embodiment, the antibody or antigen binding fragment thereof of the present invention may comprise a variable light domain ($V_L$) comprising amino acid sequence comprising:

(SEQ ID NO: 16)
DIVLTQSPASLAVSLGQRATISCRASESVDNYGISFMNWFQQKPGHP

PKLLIYGASNQGSGVPARFSGSGSGTDFSLNIHPMEEDDAAMYFCQQ

TKEVPWTFGGGTKVEIKR.

According to another embodiment, the antibody or antigen binding fragment thereof of the present invention may comprise a variable heavy domain ($V_H$) comprising amino acid sequence comprising:

(SEQ ID NO: 15)
EVQLVESGGGLVQPGGSRKLSCAASGFTFSTFGMHWVRQAPEKGLEWVAY

ISSGSSTIYYGDTLQGRFIISRDNPKNTLFLQMTSLRSEDTAMYYCARSG

YDYDPIYYALDYWGQGTSVTVSS, and a variable light domain ($V_L$) comprising amino acid sequence comprising:

(SEQ ID NO: 16)
DIVLTQSPASLAVSLGQRATISCRASESVDNYGISFMNWFQQKPGHPPKL

LIYGASNQGSGVPARFSGSGSGTDFSLNIHPMEEDDAAMYFCQQTKEVPW

TFGGGTKVEIKR.

According to other embodiments, the antibody or an antigen-binding fragment of the present invention may have sequences substantially identical to the sequences disclosed above, operable to bind to O-glycan mucin-type glycoprotein MUC16. A substantially identical sequence may comprise one or more conservative amino acid mutations. It is known in the art that one or more conservative amino acid mutation to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). According to one embodiment, these conservative amino acid mutations may be made to the framework regions of the antibody or an antigen-binding fragment while maintaining the CDR sequences listed above and the overall structure of the CDR of the antibody or fragment; thus the specificity and binding of the antibody are maintained. According to another embodiment, these conservative amino acid mutations may be made to the framework regions of the antibody or an antigen-binding fragment and the CDR sequence listed above while maintaining the antigen-binding function of the overall structure of the CDR of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or 1), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or antigen-binding fragment comprising a sequence at least 95%, 96%, 97%, 98%, or 99% identical to that of the antibodies described herein.

According to embodiment, the antibody or antigen-binding fragment thereof of the present invention may be an IgA, IgD, IgE, IgG, or IgM.

In yet another embodiment, the antibody or antigen-binding fragment thereof of the present invention may be a single-domain antibody (sdAb), or a single-chain variable fragment (scFv). According to an example, the sdAb may comprise three CDR (CDR1, 2 and 3) comprising SEQ ID NO:1, SEQ ID NO:2, and SEQ ID NO:3, respectively. In yet another example, the sdAb may comprise three CDR (CDR1, 2 and 3) comprising SEQ ID NO:4, SEQ ID NO:5, and SEQ ID NO:6, respectively.

According to an embodiment, the antibody or antigen-binding fragment thereof may be humanized or partially humanized.

According to an embodiment, the antibody or antigen-binding fragment thereof may be antibody POCmAb.

In another embodiment there is disclosed a composition comprising the antibody or antigen-binding fragment thereof of the present invention, and a pharmaceutically acceptable diluent, carrier or excipient. The composition may comprise a single antibody or antigen-binding fragment thereof of the present invention as described above, or may be a mixture of antibody or antigen-binding fragment thereof of the present invention. Furthermore, in a composition comprising a mixture of antibody or antigen-binding fragment thereof of the present invention, the antibody or antigen-binding fragment thereof may have the same specificity, or may differ in their specificities; for example, and without wishing to be limiting in any manner, the composition may comprise antibody or antigen-binding fragment thereof of the present invention specific to MUC16 (same or different epitope).

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or antigen-binding fragment. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or antigen-binding fragment to the gastrointestinal tract of the subject. Thus, the composition may comprise encapsulation, time release, or other suitable technologies for delivery of the antibody or antigen-binding fragment thereof of the present invention. It would be within the competency of a person of skill in the art to prepare suitable compositions comprising the antibody or antigen-binding fragment thereof.

In another embodiment, there is disclosed a method of inhibiting tumor growth of a tumor expressing O-glycan mucin-type glycoprotein MUC16 in a subject in need thereof, comprising administering to the subject an antibody or an antigen binding fragment thereof that targets O-glycan mucin-type glycoprotein MUC16, according to the present invention.

In an embodiment, the antibody or an antigen binding fragment thereof of the present invention is an antibody, in order for the constant domain of the antibody to be present and interact with effector cells of the immune system in order to carry out an appropriate immune response. Without wishing to be bound by theory, the Applicant believes that such interaction may be necessary for carrying out the method of the present invention. In a specific embodiment of the present invention, the antibody is a monoclonal antibody.

According to an embodiment, the O-glycan mucin-type glycoprotein MUC16 that is targeted by the antibody or an antigen binding fragment thereof comprises a truncated O-glycan, for example a truncated O-glycan that comprises a Tn antigen, a sialyl Tn antigen (STn), or a combination thereof. According to some embodiments, the antibody or an antigen binding fragment thereof of the present invention binds to a conformational epitope of tandem repeat (TR) SEA domain 5 and 6 without glycosylation of the O-glycan mucin-type glycoprotein MUC16. According to such embodiments of the present invention, targeting truncated mucin-type glycoproteins is believed to inhibit their role in tumorigenicity and tumor progression.

In embodiments, a therapeutic effective amount of the antibody or an antigen binding fragment thereof of the present invention may be used to target truncated O-glycans on the MUC16 glycoprotein, thereby inhibiting the phosphatidylinositol 3-kinase/Akt (PI3K/Akt) signaling pathway.

The present method teaches, amongst other things, that cancer specific truncation of O-glycans on the MUC16 glycoprotein (also known as CA125) creates a ligand for Her2/Neu (also known as ErbB2) receptors, which results in an oncogenic signaling cascade through Akt that increases the oncogenic potential of cancer cells. This method provides that in addition to serving as a biomarker for carcinomas, aberrant glycoforms of MUC16 can serve as a form of oncogenic cytokine.

MUC16 is a membrane bound, heavily glycosylated, cell surface glycoprotein that is expressed in normal epithelium of endometrium, trachea and cornea. The expression of MUC16 is also often upregulated in malignant tumors that also produce circulating soluble forms of MUC16. It is known that aberrant expression of membrane mucin MUC16 is associated with tumorigenicity and metastasis of cancers, such as pancreatic cancer. Further, MUC16 is not detected in pancreatic intraepithelial neoplasia (PanIN) and increased in primary tumors and metastatic lesions, suggesting that expression of this mucin is a later event in disease progression. Aberrant expression of MUC16 in ovarian cancer cells facilitates peritoneal metastasis through interactions with mesothelin (a tumor differentiation factor) and through immunosuppressive functions by blocking natural killer cell-mediated cytotoxicity. A recent study also showed that overexpression MUC16 increases breast cancer cell proliferation via stimulation of Janus Kinase 2 (JAK2). These reports strongly suggest that MUC16 plays a major role in tumor progression and metastasis through interaction with oncogenic modulators. Therefore, research suggests that MUC16 plays a major role in cancer through interaction with oncogenic modulators, however little has been done to study oligosaccharide (O-linked glycosylation) modification on mucin-type glycoproteins such as MUC16, particularly as a potential cancer therapy.

According to another embodiment, the method of the present invention may further comprise administering a second therapeutic agent comprising at least one of a cytotoxic agent, an additional antibody or a therapeutically active fragment thereof, or a chemotherapy regimen.

Indeed, it is contemplated that the present method and therapeutic strategies may be used alone or in combination with cytotoxic agents to increase overall patient survival. The cytotoxic therapeutic agents include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB (such as ErbB2) receptor inhibitors, phosphoinositide 3-kinases (PI3Ks)/Akt signaling inhibitors, mTOR inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGFIR inhibitors, matrix metalloproteinase 2 (MMP-2) inhibitors, matrix metalloproteinase 9 (MMP-9) inhibitors, thrombospondin analogs such as thrombospondin- 1 and N-Ac-Sar-Gly-Val-D-allolle-Thr-Nva-He-Arg-Pro-NHCH2CH3 or a salt thereof and analogues of N-Ac-Sar-Gly-Val-D-allolle-Thr-Nva-Ile-Arg-PrO-NHCH$_2$CH$_3$ such as N-Ac-GlyVal-D-allolle-Ser-Gln-Ile-Arg-ProNHCH2CH3 or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes, Tykerb (lapatinib) and AZD-8931 (sapitinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869 and angiozyme.

Examples of thrombospondin analogs include, but are not limited to, TSP-I and ABT-510.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-l-(4-sulfamoyl-phenyl-lH-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB (e.g. ErbB2) receptor inhibitors include, but are not limited to, CP-724-714, CI-1033, (canertinib), Herceptin (trastuzumab), Omitarg (2C4, petuzumab), TAK-165, GW-572016 (Ionafarnib), GW-282974, EKB-569, PI-166, AZD-8931 (sapitinib), dHER2 (HER2 Vaccine), APC8024 (HER2 Vaccine), anti-HER/2neu bispecific antibody, B7.her2IgG3, AS HER2 trifunctional bispecific antibodies, mAB AR-209 and mAB 2B-1.

Examles of Phosphoinositide 3-kinase inhibitor include, but are not limited to, Wortmannin, LY294002, hibiscone C, Idelalisib, Copanlisib, Duvelisib, Taselisib, Perifosine, Idelalisib, Buparlisib, Duvelisib, Alpelisib, Umbralisib, Copanlisib, PX-866, Dactolisib, CUDC-907, Voxtalisib (also known as SAR245409, XL765), CUDC-907, ME-401, IPI-549, SF1126, RP6530, INK1117, pictilisib, XL147 (also known as SAR245408), Palomid 529, GSK1059615, ZSTK474, PWT33597, IC87114, TG100-115, CAL263, RP6503, PI-103, GNE-477, and AEZS-136.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine ocfosfate, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzumab, specific CD40 antibodies and specific IGFIR antibodies, Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, ABT-751, paclitaxel, docetaxel, epothilone D (KOS-862) and ZK-EPO.

The antibodies or antigen binding fragments thereof of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy.

The antibodies or antigen binding fragments thereof of the present invention can also be used in combination with a different class of Bcl-2 inhibitors, such as ABT263 or ABT737.

According to some embodiments, the cytotoxic agent may be at least one of gemcitabine and abraxane.

According to yet another embodiment, the additional antibody or therapeutically fragment thereof may be oregovomab antibody B43.13, AR9.6 antibody, or combinations thereof.

According to an embodiment, the chemotherapy regimen may be Folfirinox.

In embodiments of the present invention, the tumor may be chosen from a pancreatic tumor, a gall bladder tumor, a gastric tumor, a colon tumor, an ovarian tumor, a breast tumor, and a liver tumor, and the method may be for the treatment of a cancer.

In another embodiment, there is disclosed a use of an antibody or an antigen binding fragment thereof that targets O-glycan mucin-type glycoprotein MUC16, according to the present invention, or of a composition according to the present invention, for inhibiting tumor growth of a tumor expressing O-glycan mucin-type glycoprotein MUC16 in a subject in need thereof.

In another embodiment, there is disclosed an antibody or an antigen binding fragment thereof that targets O-glycan mucin-type glycoprotein MUC16, according to the present invention for use in inhibiting tumor growth of a tumor expressing O-glycan mucin-type glycoprotein MUC16 in a subject in need thereof.

In another embodiment, there is disclosed an antibody or an antigen binding fragment thereof that targets O-glycan mucin-type glycoprotein MUC16, according to the present invention for use in a method of inhibiting tumor growth of a tumor expressing O-glycan mucin-type glycoprotein MUC16 in a subject in need thereof.

In another embodiment, there is disclosed a method of detection of a tumor expressing O-glycan mucin-type glycoprotein MUC16 in a subject in need thereof, comprising administering to the subject an antibody or an antigen binding fragment thereof specific to O-glycan mucin-type glycoprotein MUC16 according to the present invention and detecting the antibody or antigen binding fragment. According to an embodiment, the antibody or antigen binding fragment thereof may further comprise a detectable label, for example a fluorescent marker, a radioactive marker, an MRI contrast agent, or combinations thereof, as is known in the art.

The invention also encompasses nucleic acid vector comprising a nucleotide sequence encoding a the antibody or antigen binding fragment thereof of the present invention, as well as cells comprising the nucleic acid vector, for expressing the the antibody or antigen binding fragment thereof of the present invention, and cells for expressing the the antibody or antigen binding fragment thereof of the present invention.

The present invention will be more readily understood by referring to the following examples which are given to illustrate the invention rather than to limit its scope.

EXAMPLE 1

Expression of MUC16 Fragment

An expression vector encoding a fragment of MUC16 (the TR 1.2 construct) which comprises MUC16 tandem repeat (TR) SEA domain 5 and 6 (SEQ ID NO:17). This fragment contains SEA domain of TR 5, along with the PST rich sequences of TR 4 on one side and TR6 on the other side. The TR1.2 MUC16 fragment was expressed in CHO cells and purified according to standard techniques.

EXAMPLE 2

Anti-MUC16 Monoclonal Antibody Generation

Animal immunization. Four six-week old female A/J mice (The Jackson Laboratory, Bar Harbor, Me.) were bled (pre-immune serum) and injected intraperitoneally and subcutaneously with 100 μg of the TR1.2 MUC16 antigen emulsified in Titermax adjuvant at day 0 and at day 21. Blood was collected in microvette CB 300Z at day 31 or 38, and serum was stored at −20° C. until further use.

ELISA (serum titer determination). Pre- and post-immune sera titers of animals were assessed by ELISA. Unless otherwise stated, all incubations were performed at room temperature. Briefly, half-area 96-well were coated with 25 μl per well of immunogen at 20 μg/ml in PBS and incubated overnight at 4° C. Microplates were washed three times in PBS and blocked for 30 min with PBS containing 1% bovine serum albumin (BSA). Blocking buffer was removed and 25 μl of serial dilutions of sera samples were added. After a 2-h incubation, microplates were washed 4 times with PBS-Tween 20 0.05% and 25 μl of a 1/5,000 dilution of alkaline phosphatase conjugated goat anti-mouse IgG (H+L) in blocking buffer was added. After a 1-h incubation, microplates were washed 4 times and 25 μl of p-nitrophenyl phosphate (pNPP) substrate at 1 mg/ml in carbonate buffer at pH 9.6 was added and further incubated for 30 min. Absorbance was read at 405 nm using a plate reader. All pre-immune bleeds were negative and all post-immune bleeds were very strong (above 1/12800) on recombinant protein. A final intraperitoneal booster injection using 100 μg of recombinant protein in PBS was done 3 days prior to fusion experiment.

Fusion of the harvested spleen cells. All manipulations were done under sterile conditions. Spleen cells were harvested in Iscove's Modified Dulbecco's medium (IMDM) and fused to NS0 myeloma cell line using polyethylene glycol. Spleen cells and myeloma cells were washed in IMDM, counted in RBC lysing buffer and mixed together at a 5:1 ratio. Pelleted cells were fused together by adding 1 ml of a 50% solution of PEG 4000 in PBS preheated at 37° C. drop-wise over one minute, and incubated at 37° C. for an additional 90 sec. The reaction was stopped by addition of 30 ml of IMDM at 22° C. over 2 min. After a 10 min incubation, freshly fused cells were spun for 10 min. Cells were washed once in IMDM supplemented with 10% heat inactivated FBS and suspended at a concentration of $2 \times 10^5$ input myeloma cells per ml in HAT selection medium (IMDM containing 20% heat inactivated FBS, penicillin-streptomycin, 1 ng/ml mouse IL-6, HAT media supplement and L-glutamine and incubated at 37° C., 5% $CO_2$. The next day, hybridoma cells were washed and suspended at a concentration of $2 \times 10^5$ input myeloma cells per ml in semi-solid medium D (StemCell Technologies®) supplemented with 5% heat inactivated FBS, 1 ng/ml mouse IL-6 and 10 μg/ml FITC-F(ab')2 Goat anti-mouse IgG. The cell mixture was plated in Omnitray® dish and further incubated for 6-7 days at 37° C., 5% $CO_2$. Fluorescent secretor clones were then transferred using a mammalian cell clone picker into sterile 96-w plates containing 200 μl of IMDM supplemented with 20% heat inactivated FBS, penicillin-streptomycin, 1 ng/ml mouse IL-6, HT media supplement (Sigma® Cat# H0137) and L-glutamine and incubated for 2-3 days at 37° C., 5% CO2.

Screening. Hybridoma supernatant were screened by ELISA to detect specific binders. To this end, 96-wells half-area plates were coated with 25 μl of TR1.2 MUC16 at 20 μg/ml or an irrelevant control protein at 5 μg/ml in PBS and incubated overnight at 4° C. Microplates were washed 3 times with PBS, blocked with PBS-BSA 1%, and 25 μl of hybridoma supernatant were added and incubated at 37° C., 5% $CO_2$ for 2 hours. Plates were washed 4 times with PBS-Tween 20 0.05% and incubated for one hour at 37° C., 5% $CO_2$ with 25 μl of secondary antibody alkaline phosphatase conjugated F(ab')2 goat anti-mouse IgG diluted 1/5000 in blocking buffer. After 4 washes with PBS-Tween 20 0.05%, 25 μl of a 1 mg/ml pNPP substrate solution was added and further incubated for one hour at 37° C. OD405 nm measurements were done using a microplate reader. Hits were confirmed using alkaline phosphatase conjugated F(ab')2 goat anti-mouse IgG Fc gamma specific and 50 mAbs were selected for further characterization.

Recloning of hybridomas. Selected hybridoma were recloned by limiting dilution to ensure their monoclonality.

EXAMPLE 3

Making of Recombinant Anti-MUC16

The $V_H$ and $V_L$ regions of the candidate antibody against MUC16 TR1.2A were sequenced, synthesized and cloned into the pTT5 vector in-frame with a constant domain of a human IgG1 heavy chain (comprising CH1, CH2 and CH3 regions) or in-frame with a constant domain of a human kappa light chain -, and recombinant mAbs were produced in CHO-3E7 cells by transient transfection according to Delafosse et al. J Biotechnol, 227 (2016). This antibody was named POCmAb.

TABLE 1

Amino acid sequence of V$_H$ and V$_L$ regions of antibody P0CmAb

| Region | Sequence | SEQ ID NO |
|---|---|---|
| V$_H$ | EVQLVESGGGLVQPGGSRKLSCAASGFTFSTFGMHWVRQAPEKG LEWVAYISSGSSTIYYGDTLQGRFIISRDNPKNTLFLQMTSLRS EDTAMYYCARSGYDYDPIYYALDYWGQGTSVTVSS | SEQ ID NO: 15 |
| V$_L$ | DIVLTQSPASLAVSLGQRATISCRASESVDNYGISFMNWFQQKP GHPPKLLIYGASNQGSGVPARFSGSGSGTDFSLNIHPMEEDDAA MYFCQQTKEVPWTFGGGTKVEIKR | SEQ ID NO: 16 |

TABLE 2

Chothia numbering of the V$_H$ sequence
=scheme number. sequence position. amino acid

| | | |
|---|---|---|
| H1 | 1 | E |
| H2 | 2 | V |
| H3 | 3 | Q |
| H4 | 4 | L |
| H5 | 5 | V |
| H6 | 6 | E |
| H7 | 7 | S |
| H8 | 8 | G |
| H9 | 9 | G |
| H10 | 10 | G |
| H11 | 11 | L |
| H12 | 12 | V |
| H13 | 13 | Q |
| H14 | 14 | P |
| H15 | 15 | G |
| H16 | 16 | G |
| H17 | 17 | S |
| H18 | 18 | R |
| H19 | 19 | K |
| H20 | 20 | L |
| H21 | 21 | S |
| H22 | 22 | C |
| H23 | 23 | A |
| H24 | 24 | A |
| H25 | 25 | S |
| H26 | 26 | G |
| H27 | 27 | F |
| H28 | 28 | T |
| H29 | 29 | F |
| H30 | 30 | S |
| H31 | 31 | T |
| H32 | 32 | F |
| H33 | 33 | G |
| H34 | 34 | M |
| H35 | 35 | H |
| H36 | 36 | W |
| H37 | 37 | V |
| H38 | 38 | R |
| H39 | 39 | Q |
| H40 | 40 | A |
| H41 | 41 | P |
| H42 | 42 | E |
| H43 | 43 | K |
| H44 | 44 | G |
| H45 | 45 | L |
| H46 | 46 | E |
| H47 | 47 | W |
| H48 | 48 | V |
| H49 | 49 | A |
| H50 | 50 | Y |
| H51 | 51 | I |
| H52 | 52 | S |
| H52A | 53 | S |
| H53 | 54 | G |
| H54 | 55 | S |
| H55 | 56 | S |
| H56 | 57 | T |
| H57 | 58 | I |
| H58 | 59 | Y |
| H59 | 60 | Y |
| H60 | 61 | G |
| H61 | 62 | D |
| H62 | 63 | T |
| H63 | 64 | L |
| H64 | 65 | Q |
| H65 | 66 | G |
| H66 | 67 | R |
| H67 | 68 | F |
| H68 | 69 | I |
| H69 | 70 | I |
| H70 | 71 | S |
| H71 | 72 | R |
| H72 | 73 | D |
| H73 | 74 | N |
| H74 | 75 | P |
| H75 | 76 | K |
| H76 | 77 | N |
| H77 | 78 | T |
| H78 | 79 | L |
| H79 | 80 | F |
| H80 | 81 | L |
| H81 | 82 | Q |
| H82 | 83 | M |
| H82A | 84 | T |
| H82B | 85 | S |
| H82C | 86 | L |
| H83 | 87 | R |
| H84 | 88 | S |
| H85 | 89 | E |
| H86 | 90 | D |
| H87 | 91 | T |
| H88 | 92 | A |
| H89 | 93 | M |
| H90 | 94 | Y |
| H91 | 95 | Y |
| H92 | 96 | C |
| H93 | 97 | A |
| H94 | 98 | R |
| H95 | 99 | S |
| H96 | 100 | G |
| H97 | 101 | Y |
| H98 | 102 | D |
| H99 | 103 | Y |
| H100 | 104 | D |
| H100A | 105 | P |
| H100B | 106 | I |
| H100C | 107 | Y |
| H100D | 108 | Y |
| H100E | 109 | A |
| H100F | 110 | L |
| H101 | 111 | D |
| H102 | 112 | Y |
| H103 | 113 | W |
| H104 | 114 | G |
| H105 | 115 | Q |
| H106 | 116 | G |
| H107 | 117 | T |
| H108 | 118 | S |
| H109 | 119 | V |
| H110 | 120 | T |

TABLE 2-continued

Chothia numbering of the $V_H$ sequence
=scheme number. sequence position. amino acid

| | | |
|---|---|---|
| H111 | 121 | V |
| H112 | 122 | S |
| H113 | 123 | S |

TABLE 3

CDR Sequences (Chothia), and CDR Canonical Class

| Region | Sequence | Residues | Length | SEQ ID NO |
|---|---|---|---|---|
| HFR1 | EVQLVESGGGLVQPGGSRKLSCAAS | 1-25 | 25 | SEQ ID NO: 7 |
| CDR H1 | GFTFSTF | 26-32 | 7 | SEQ ID NO: 1 |
| HFR2 | GMHWVRQAPEKGLEWVAYI | 33-51 | 19 | SEQ ID NO: 8 |
| CDR H2 | SSGSST | 52-57 | 6 | SEQ ID NO: 2 |
| HFR3 | IYYGDTLQGRFIISRDNPKNTLFLQMTSLRSEDTAMYYCAR | 58-98 | 41 | SEQ ID NO: 9 |
| CDR H3 | SGYDYDPIYYALDY | 99-112 | 14 | SEQ ID NO: 3 |
| HFR4 | WGQGTSVTVSS | 113-123 | 11 | SEQ ID NO: 10 |

CDR H1 is predicted to be canonical class 1 (1/10A)
CDR H2 is predicted to be canonical class 3 (3/10B)

TABLE 4

Chothia numbering of the $V_L$ sequence
=scheme number. sequence position. amino acid

| | | |
|---|---|---|
| L1 | 1 | D |
| L2 | 2 | I |
| L3 | 3 | V |
| L4 | 4 | L |
| L5 | 5 | T |
| L6 | 6 | Q |
| L7 | 7 | S |
| L8 | 8 | P |
| L9 | 9 | A |
| L10 | 10 | S |
| L11 | 11 | L |
| L12 | 12 | A |
| L13 | 13 | V |
| L14 | 14 | S |
| L15 | 15 | L |
| L16 | 16 | G |
| L17 | 17 | Q |
| L18 | 18 | R |
| L19 | 19 | A |
| L20 | 20 | T |
| L21 | 21 | I |
| L22 | 22 | S |
| L23 | 23 | C |
| L24 | 24 | R |
| L25 | 25 | A |
| L26 | 26 | S |
| L27 | 27 | E |
| L28 | 28 | S |
| L29 | 29 | V |
| L30 | 30 | D |
| L30A | 31 | N |
| L30B | 32 | Y |
| L30C | 33 | G |
| L30D | 34 | I |
| L31 | 35 | S |
| L32 | 36 | F |
| L33 | 37 | M |
| L34 | 38 | N |
| L35 | 39 | W |
| L36 | 40 | F |
| L37 | 41 | Q |
| L38 | 42 | Q |
| L39 | 43 | K |
| L40 | 44 | P |
| L41 | 45 | G |
| L42 | 46 | H |
| L43 | 47 | P |
| L44 | 48 | P |
| L45 | 49 | K |
| L46 | 50 | L |
| L47 | 51 | L |
| L48 | 52 | I |
| L49 | 53 | Y |
| L50 | 54 | G |
| L51 | 55 | A |
| L52 | 56 | S |
| L53 | 57 | N |
| L54 | 58 | Q |
| L55 | 59 | G |
| L56 | 60 | S |
| L57 | 61 | G |
| L58 | 62 | V |
| L59 | 63 | P |
| L60 | 64 | A |
| L61 | 65 | R |
| L62 | 66 | F |
| L63 | 67 | S |
| L64 | 68 | G |
| L65 | 69 | S |
| L66 | 70 | G |
| L67 | 71 | S |
| L68 | 72 | G |
| L69 | 73 | T |
| L70 | 74 | D |
| L71 | 75 | F |
| L72 | 76 | S |
| L73 | 77 | L |
| L74 | 78 | N |
| L75 | 79 | I |
| L76 | 80 | H |
| L77 | 81 | P |
| L78 | 82 | M |
| L79 | 83 | E |
| L80 | 84 | E |

TABLE 4-continued

Chothia numbering of the $V_L$ sequence
=scheme number. sequence position. amino acid

| | | |
|---|---|---|
| L81 | 85 | D |
| L82 | 86 | D |
| L83 | 87 | A |
| L84 | 88 | A |
| L85 | 89 | M |
| L86 | 90 | Y |
| T87 | 91 | F |
| L88 | 92 | C |
| L89 | 93 | Q |
| L90 | 94 | Q |
| L91 | 95 | T |
| L92 | 96 | K |
| L93 | 97 | E |
| L94 | 98 | V |
| L95 | 99 | P |
| L96 | 100 | W |
| L97 | 101 | T |
| L98 | 102 | F |
| L99 | 103 | G |
| L100 | 104 | G |
| L101 | 105 | G |
| L102 | 106 | T |
| L103 | 107 | K |
| L104 | 108 | V |
| L105 | 109 | E |
| L106 | 110 | I |
| L107 | 111 | K |
| L108 | 112 | R |

TABLE 5

Sequences (Chothia), and CDR Canonical Class

| Region | Sequence | Residues | Length | SEQ ID NO |
|---|---|---|---|---|
| LFR1 | DIVLTQSPASLAVSLGQRATISC | 1-23 | 23 | SEQ ID NO: 11 |
| CDR L1 | RASESVDNYGISFMN | 24-38 | 15 | SEQ ID NO: 4 |
| LFR2 | WFQQKPGHPPKLLIY | 39-53 | 15 | SEQ ID NO: 12 |
| CDR L2 | GASNQGS | 54-60 | 7 | SEQ ID NO: 5 |
| LFR3 | GVPARFSGSGSGTDFSLNIHPMEEDDAAMYFC | 61-92 | 32 | SEQ ID NO: 13 |
| CDR L3 | QQTKEVPWT | 93-101 | 9 | SEQ ID NO: 6 |
| LFR4 | FGGGTKVEIKR | 102-112 | 11 | SEQ ID NO: 14 |

CDR L1 has no canonical class match
CDR L2-Class 1
CDR L3-Class 1

EXAMPLE 4

Binding Specificity of Anti-MUC16 TR1.2A

Figures 3A, 3B:
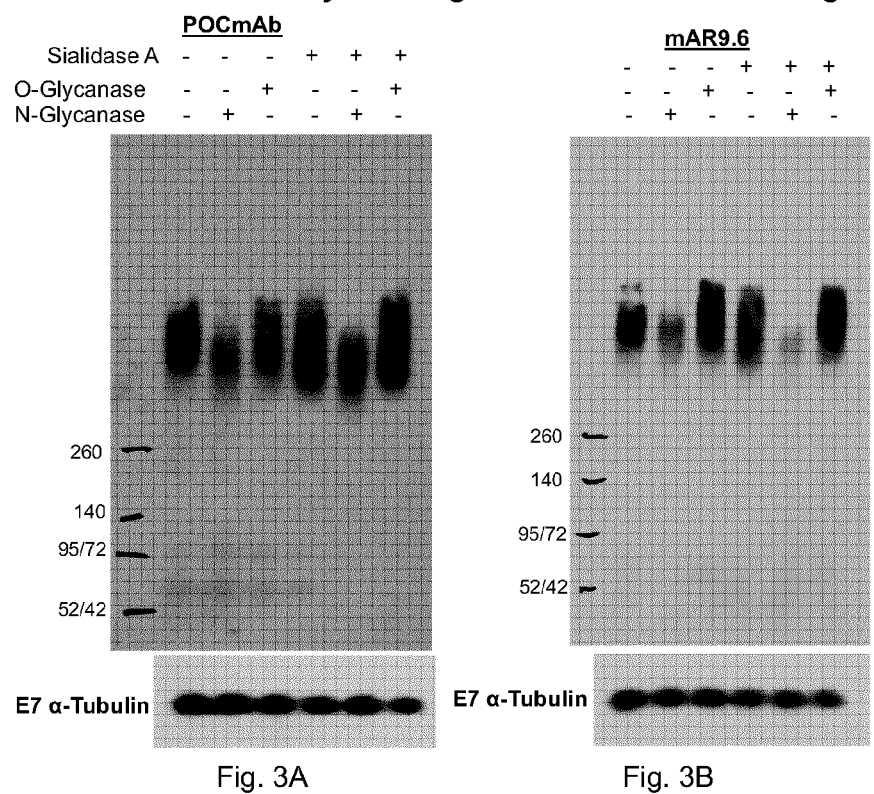
FIG. 3A illustrates the binding specificity of humanized (POCmAb) antibody to pancreatic cancer cells treated with sialidase, O-glycanase and N-glycanase glycosidases.
FIG. 3B illustrates the binding specificity of murine (mAR9.6) antibodies to pancreatic cancer cells treated with sialidase, O-glycanase and N-glycanase glycosidases.
Figure 4:
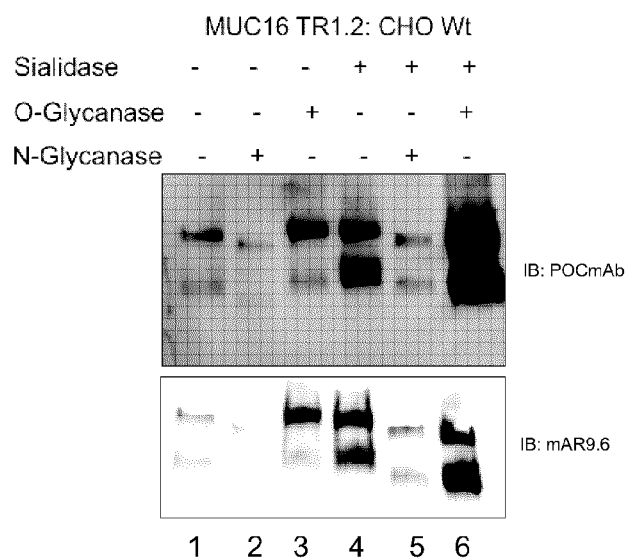
FIG. 4 illustrates the binding specificity of humanized (POCmAb) or murine (mAR9.6) antibodies to MUC16 TR1.2 purified from WT CHO cells treated with sialidase, O-glycanase and N-glycanase glycosidases.
Figure 5A:
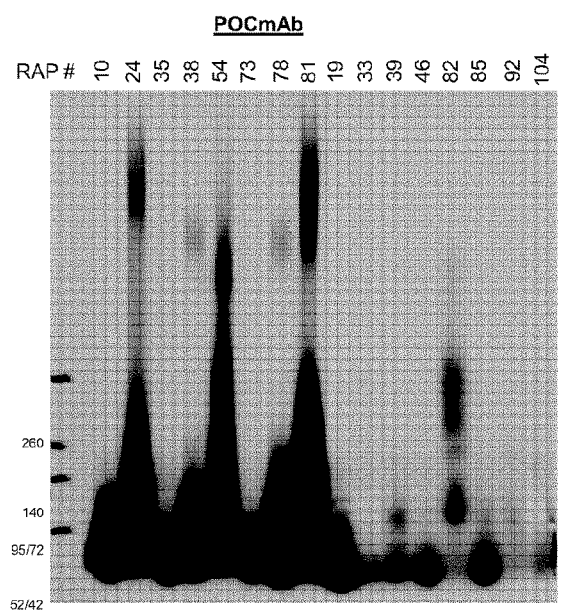
FIG. 5A illustrates the binding specificity of humanized (POCmAb) antibody to pancreatic cancer patients ascites fluid samples.
Figure 5B:
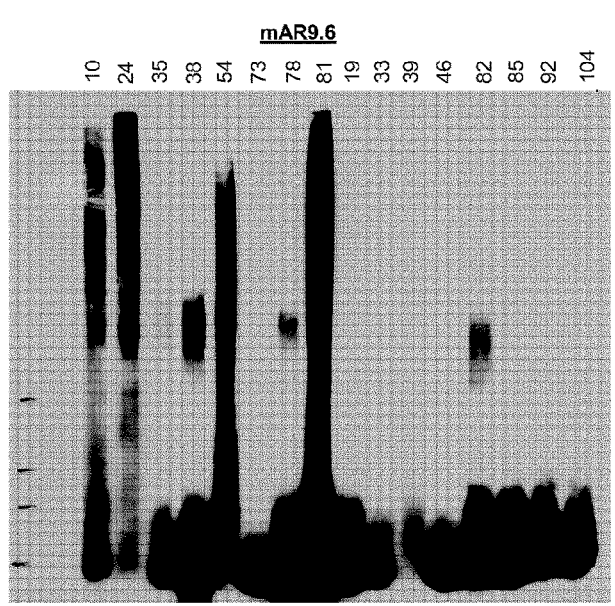
FIG. 5B illustrates the binding specificity of murine (mAR9.6) antibodies to pancreatic cancer patients ascites fluid samples.

Now referring to FIG. 2. The binding specificity of humanized version of the anti-MUC16 TR1.2A, namely (POCmAb) against various pancreatic cancer cells is tested. FIG. 2A shows that POCmAb recognizes various isoforms of MUC16 in different pancreatic cancer cells as compared to another anti-MUC16 antibody, mouse anti-MUC16 mAb AR9.6 (also referred to as mAR9.6; FIG. 2B). Next, the binding specificity of murine mAR9.6 and humanized POCmAb anti-MUC16 antibodies against human pancreatic cancer cells (T3M4) that are treated with Sialidase, O-glycanase and N-glycanase enzymes is tested. FIGS. 3A and 3B shows that samples treated with N-glycanase have reduced reactivity with either antibodies (lanes 2 and 5). However, samples treated with O-glycanase and sialidase either alone or in combination shows increased reactivity with either antibodies (lanes 3, 4 and 6). Next, the binding specificity of murine mAR9.6 and humanized POCmAb anti-MUC16 antibodies against MUC16 TR1.2 purified from CHO wild-type cells, which was treated with different glycosidases such as sialidase, O-glycanase and N-glycanase was tested. FIG. 4 shows that samples treated with N-glycanase have reduced reactivity with either antibodies (lanes 2 and 5). However, samples treated with O-glycanase and sialidase either alone or in combination show that increased reactivity with either antibodies (lanes 3, 4 and 6). Taken together, these results suggest that N-glycans on the MUC16 glycoprotein is essential for antibody binding. However, O-glycans and sialic acid groups on the MUC16 either blocks or mask the epitopes for anti-MUC16 antibody reactivity. FIG. 5A shows that POCmAb recognizes various isoforms of MUC16 in Pancreatic Ductal Adenocarcinoma (PDAC) patients ascites fluids (37.5%; 6/16) than compared to mouse anti-MUC16 mAb AR9.6 (FIG. 5B).

EXAMPLE 4

Live/Dead Cell Cytotoxicity Assay

Live/Dead cytotoxicity assay is performed to compare the effect of mAR9.6 and POCmAb antibodies in inducing cell death in PDAC cells. Mouse AR9.6 antibody has affinity and specific reactivity towards MUC16, which enables it to inhibit in vivo pancreatic tumor growth and metastasis. mAb AR9.6 significantly induced cell death of PDAC cells and selectively inhibited the activation of oncogenic signaling.

Materials and Methods. T3M4 wildtype (WT) and COSMC deleted (SimpleCells, SC) were treated with equal amounts of mAR 9.6 (5 µg/ml) and POCmAb (5 µg/ml) or with isotype matched (either mouse or human) control IgG antibody for 24 h. For the comparison of effect of antibodies in inducing cell death, T3M4 WT cells were treated with Sapitinib (an ErbB receptor tyrosine kinase inhibitor, 5.4 µM) and LY294002 (PI3K/Akt inhibitor, 11.3 µM) alone or in combination with mAR9.6 (5 µg/ml) and POCmAb (5 µg/ml) for 24 h. The cells were washed well with cell-culture grade PBS. 20 µl ethidium homodimer-1 (EthD-1, 2 mM) was dissolved in 10 ml PBS. To this solution, 5 µl of calcein acetoxymethyl ester (calcein-AM, 4 mM) was added. 150 µl of this combined reagent was added to the cells grown on coverslip and incubated for 30-45 minutes. The numbers of live and dead cells were detected with Zeiss LSM 710™ confocal laser scanning microscope (Carl Zeiss, Inc., Thornwood, NY, USA) at Confocal Laser Scanning Fluorescence Microscope Core Facility, UNMC. The ratio of dead cells to total cells was calculated for quantitative comparisons. Unpaired Student's t-test was performed to calculate the statistical significance between the antibodies treated T3M4 WT and T3M4 SC cells (n=4) ($p<0.05$ considered statistically significant). Two way analysis of variance (ANOVA) was performed to calculate the statistical significance between the inhibitors and antibody treated T3M4 cells (n=4) ($p<0.05$ considered statistically significant).

Figure 6:
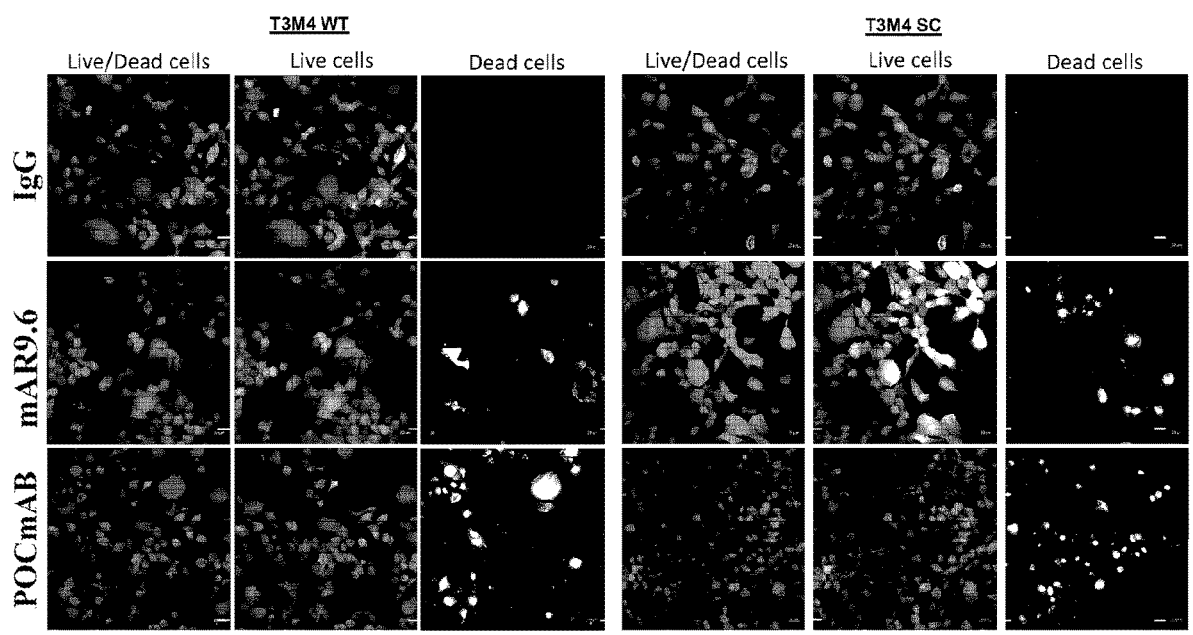
FIG. 6 illustrates the results of the treatment of T3M4 WT and SC cells with a control IgG antibody, mAR9.6 monoclonal antibody, and the POCmAb monoclonal antibody of the present invention. The left column represents merged images of the live and dead cells, the center column the live cells and the right column the dead cells.
Figure 7:
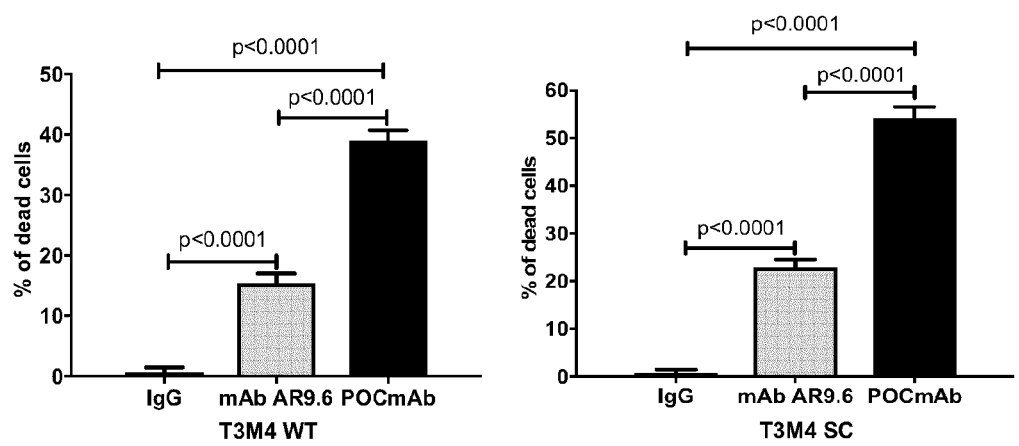
FIG. 7 illustrates the quantification of cell death pursuant to the treatment described in FIG. 6.
Figure 8:
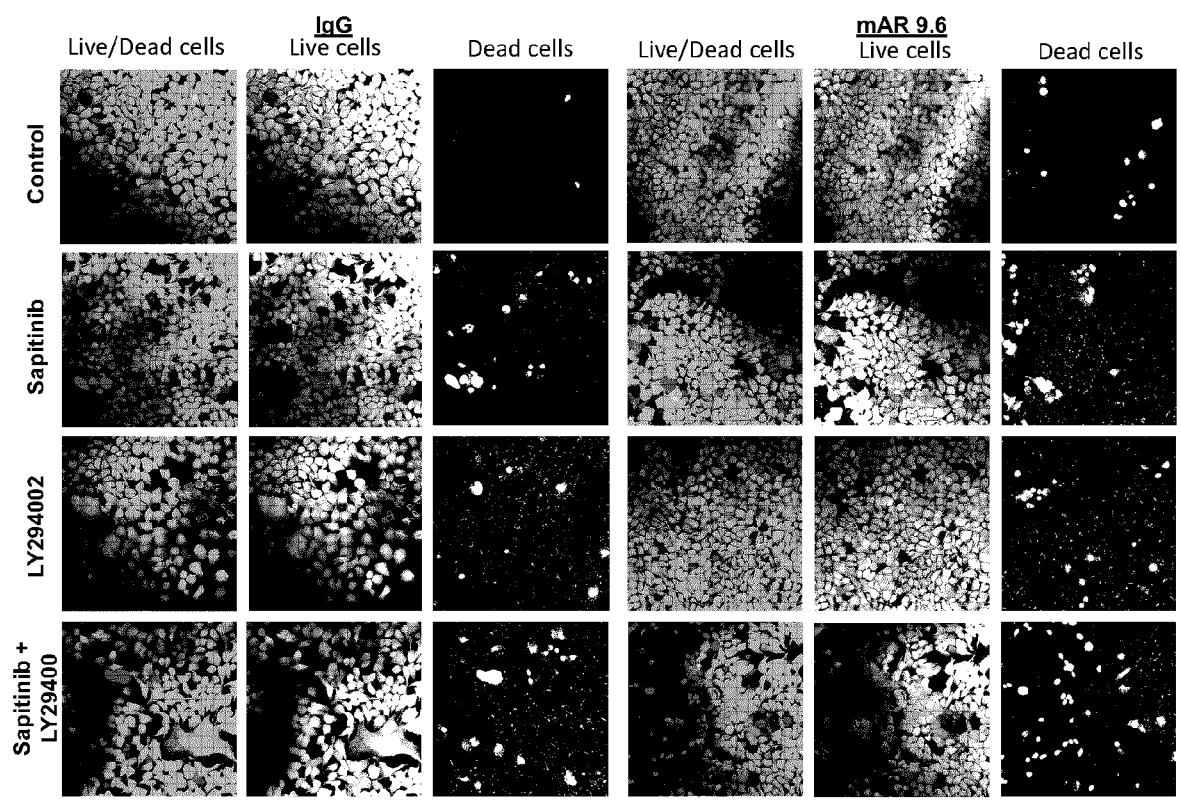
FIG. 8 illustrates the results of the treatment of T3M4 WT cells with either 1) a control IgG antibody; 2) mAR9.6 monoclonal antibody; 3) Sapitinib with either control IgG or mAR9.6; 4) LY294002 with either control IgG or mAR9.6; and 5) a combination of Sapitinib and LY294002 with either control IgG or mAR9.6. The left column represents merged images of the live and dead cells, the center column the live cells and the right column the dead cells.

Results—Monoclonal antibodies mAR9.6 and POCmAb inducing cell death in PDAC cells. T3M4 wildtype (WT) and COSMC deleted (SimpleCells, SC) were treated with mAR 9.6 (5µg/ml), POCmAb (5 µg/ml), or an isotype matched control IgG antibody for 24 h. The effect of antibodies in inducing cell death in T3M4 WT and SC cells were analyzed by Live/Dead cytotoxicity assay. As shown in the FIGS. 6 and 7, the live cells were stained in green and the dead cells in red. Both antibodies mAR 9.6 ($p<0.0001$) and POCmAb ($p<0.0001$) were found to induce cell death significantly in T3M4 WT cells when compared to either mouse or human IgG control. While comparing the effect between antibodies in inducing cell death, POCmAb was found to be more effective than mAR9.6 (about 39% vs. 15%; $p<0.0001$). COSMC deleted T3M4 cells are highly tumorigenic cells as they express a number of truncated O-glycans on their surface. Interestingly, both the antibodies induced more cell death in T3M4 SC cells. POCmAb induced cell death was significantly higher in T3M4 SC cells when compared to mAR9.6 antibody induced cell death (about 55% vs. 22%; $p<0.0001$).

Figure 9:
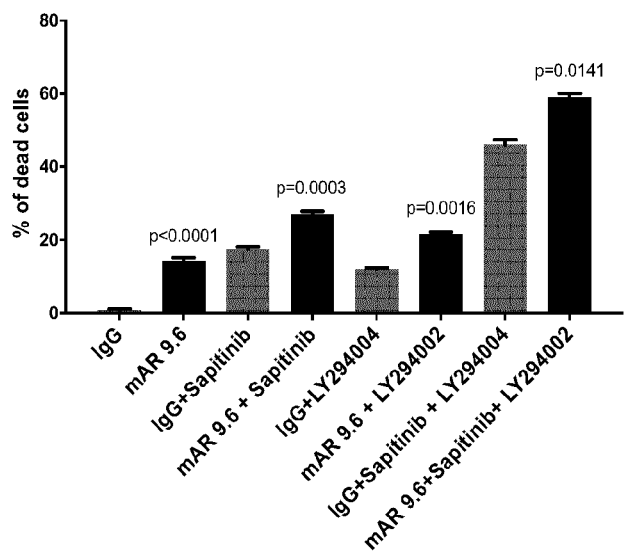
FIG. 9 illustrates quantification of cell death pursuant to each the treatment conditions described in FIG. 8.
Figure 10:
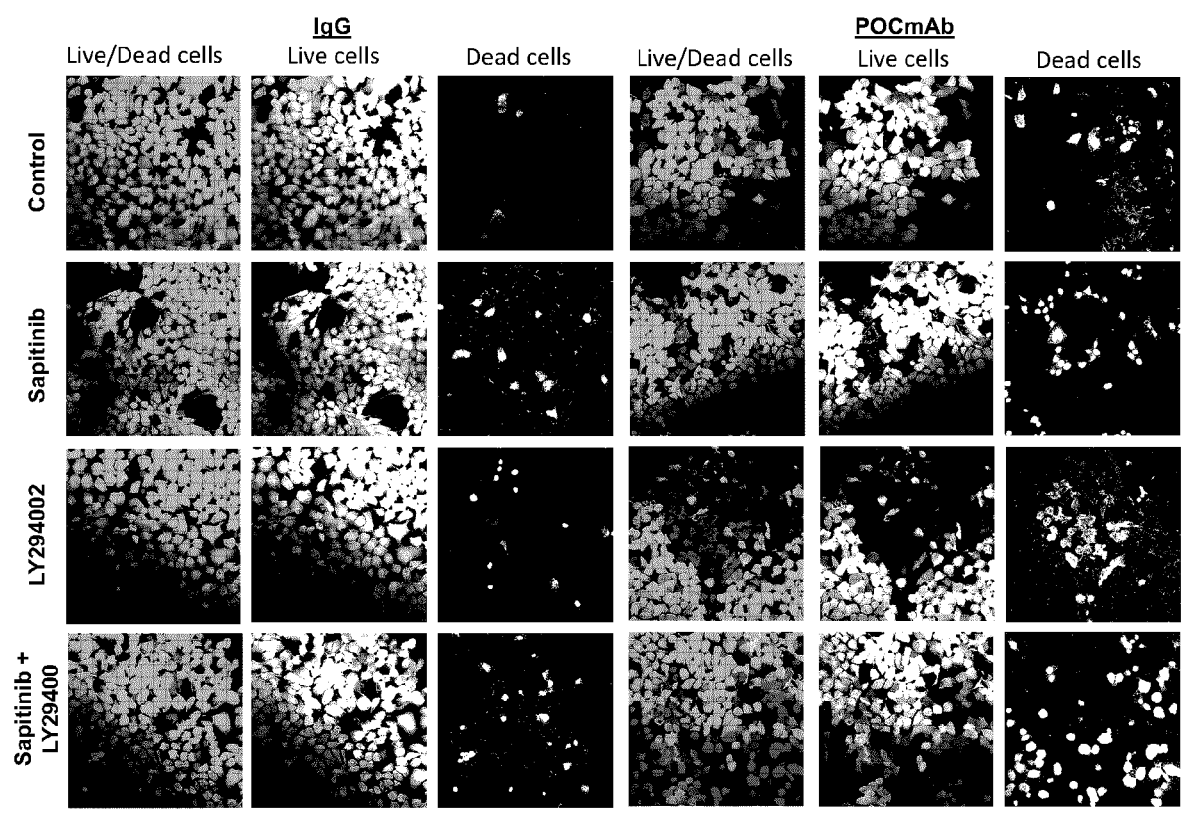
FIG. 10 illustrates the results of the treatment of T3M4 WT cells with either 1) a control IgG antibody; 2) POCmAb monoclonal antibody; 3) Sapitinib with either control IgG or POCmAb; 4) LY294002 with either control IgG or POCmAb; and 5) a combination of Sapitinib and LY294002 with either control IgG or POCmAb. The left column represents merged images of the live and dead cells, the center column the live cells and the right column the dead cells.

As an additional comparison of the effect of POCmAb antibody versus mAR9.6 in inducing cell death, T3M4 cells treated with Sapitinib (an ErbB receptor tyrosine kinase inhibitor, 5.4 µM) and LY294002 (PI3K/Akt inhibitor, 11.3 µM) alone or in combination with mAR9.6 (5 µg/ml) and POCmAb (5 µg/ml), or an isotype matched control IgG antibody for 24 h. As shown in FIGS. 9-10, the combination therapy of mAR9.6 induced significant cell death in T3M4 cells as compared to inhibitor alone treated cells. mAR9.6 along with Sapitinib induced more cell death when compared to sapitinib and mouse IgG treated cells (about 17% vs. about 27%, $p=0.0003$). Similarly, mAR9.6 along with LY294002 induced more cell death when compared to LY294002 and mouse IgG treated cells (about 15% vs. about about 21%, $p=0.0016$). More interestingly, the combination of mAR9.6 and Sapitinib along with LY294002 further induced more cell death when compared to Sapitinib and LY294002 and mouse IgG treated cells (about 43% vs. about 59%, $p=0.0141$). The results of this study shown that mAR9.6 in combinations with Sapitinib and LY294002 is highly effective in inducing cell death in PDAC cells.

Figure 11:
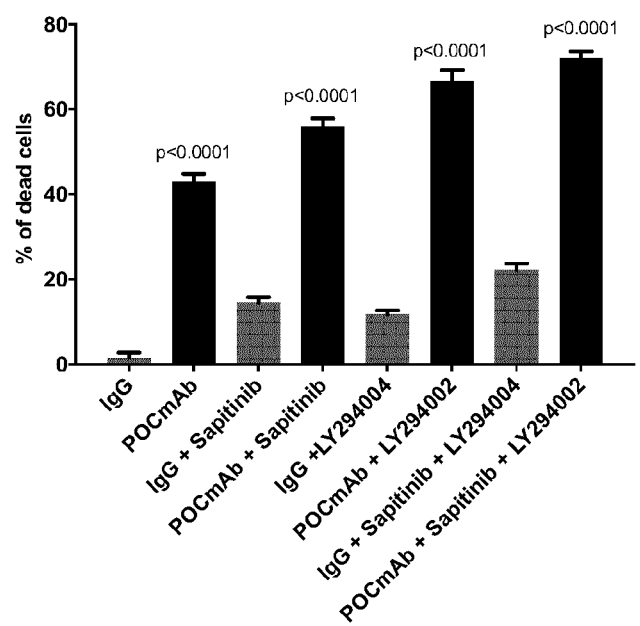
FIG. 11 illustrates the quantification of cell death pursuant to each the treatment conditions described in FIG. 10.
Figure 12:
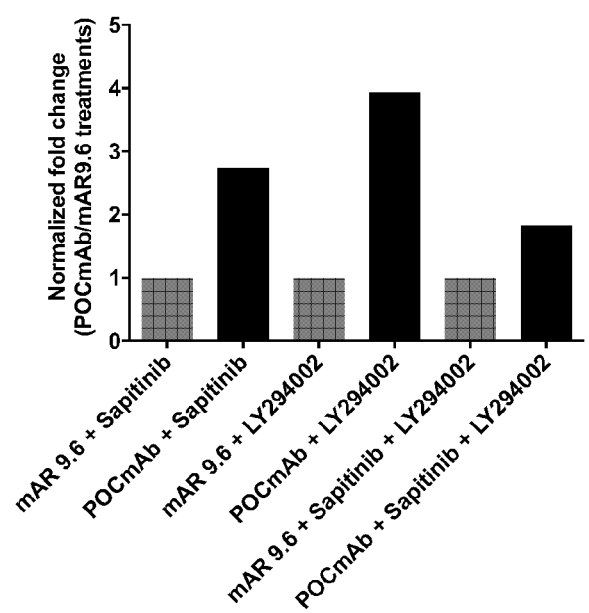
FIG. 12 illustrates the normalized fold-change based on the results presented in FIGS. 8 to 11, that show that the POCmAb antibody was found to be unexpectedly and surprisingly more effective than the mAR9.6 antibody in inducing cell death in PDAC cells.

Cells were also treated with POCmAb either alone or in combination with Sapitinib or LY294002. Now referring to FIGS. 10-11, it is shown that POCmAb along with Sapitinib induced significantly increased number of cell death when compared to sapitinib and human IgG treated cells (about 17% vs. about 55%, $p<0.0001$). Similarly, POCmAb along with LY294002 induced significantly increased number of cell death when compared to LY294002 and human IgG treated cells (about 15% vs. about 65%, $p<0.0001$). More interestingly, the combination of POCmAb with Sapitinib and LY294002 further induced significantly more cell death when compared to Sapitinib and LY294002 and human IgG treated cells (about 20% vs. about 70%, $p<0.0001$). Taken together, while comparing the effect of mAR9.6 vs. POCmAb antibodies in inducing cell death in PDAC cells, POCmAb antibody was found to be unexpectedly and surprisingly more effective (FIG. 12).

While preferred embodiments have been described above and illustrated in the accompanying drawings, it will be evident to those skilled in the art that modifications may be made without departing from this disclosure. Such modifications are considered as possible variants comprised in the scope of the disclosure.

SEQUENCES

| SEQ ID NO: | Sequence | Description |
| --- | --- | --- |
| SEQ ID NO: 1 | GFTFSTF | CDR H1 |
| SEQ ID NO: 2 | SSGSST | CDR H2 |
| SEQ ID NO: 3 | SGYDYDPIYYALDY | CDR H3 |
| SEQ ID NO: 4 | RASESVDNYGISFMN | CDR L1 |
| SEQ ID NO: 5 | GASNQGS | CDR L2 |
| SEQ ID NO: 6 | QQTKEVPWT | CDR L3 |
| SEQ ID NO: 7 | EVQLVESGGGLVQPGGSRKLSCAAS | HFR 1 |
| SEQ ID NO: 8 | GMHWVRQAPEKGLEWVAYI | HFR 2 |
| SEQ ID NO: 9 | IYYGDTLQGRFIISRDNPKNTLFLQMTSLRSEDTAMYYCAR | HFR 3 |
| SEQ ID NO: 10 | WGQGTSVTVSS | HFR 4 |
| SEQ ID NO: 11 | DIVLTQSPASLAVSLGQRATISC | LFR 1 |
| SEQ ID NO: 12 | WFQQKPGHPPKLLIY | LFR 2 |
| SEQ ID NO: 13 | GVPARFSGSGSGTDFSLNIHPMEEDDAAMYFC | LFR 3 |
| SEQ ID NO: 14 | FGGGTKVEIKR | LFR 4 |

-continued

SEQUENCES

| SEQ ID NO: | Sequence | Description |
|---|---|---|
| SEQ ID NO: 15 | EVQLVESGGGLVQPGGSRKLSCAASGFTFSTFGMHWVRQAPEK GLEWVAYISSGSSTIYYGDTLQGRFIISRDNPKNTLFLQMTSL RSEDTAMYYCARSGYDYDPIYYALDYWGQGTSVTVSS | variable heavy domain (VH) |
| SEQ ID NO: 16 | DIVLTQSPASLAVSLGQRATISCRASESVDNYGISFMNWFQQK PGHPPKLLIYGASNQGSGVPARFSGSGSGTDFSLNIHPMEEDD AAMYFCQQTKEVPWTFGGGTKVEIKR | variable light domain (VL) |
| SEQ ID NO: 17 | IPVPTSSTPGTSTVDLGSGTPSSLPSPTTAGPLLVPFTLNFTI TNLKYEEDMHCPGSRKFNTTERVLQSLLGPMFKNTSVGPLYSG CRLTLLRSEKDGAATGVDAICTHRLDPKSPGVDREQLYWELSQ LTNGIKELGPYTLDRNSLYVNGFTHQTSAPNTSTPGTSTVDLG TSGTPSSLPSPTSAGPLLVPFT | MUC16 1.2TR |

REFERENCES

1. Arbabi-Ghahroudi, M., Desmyter, A., Wyns, L., Hamers, R., Muyldermans, S. (1997) *FEBS Lett* 414:521-6.
2. Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., MacKenzie, R., Zhang, J. (2010) *Cancer Lett* 289:81-90.
3. Chothia, C., Lesk, A. M. (1987) *J Mol Biol* 196:901-17.
4. Davies, J., Riechmann, L. (1996) *Immunotechnology* 2:169-79.
5. de Kruif, J., Logtenberg, T. (1996) *J Biol Chem* 271:7630-4.
6. Dumoulin, M., Conrath, K., Van Meirhaeghe, A., Meersman, F., Heremans, K., Frenken, L. G., Muyldermans, S., Wyns, L., Matagne, A. (2002) *Protein Sci* 11:500-15.
7. Durocher, Y., Perret, S., Kamen, A. (2002 *Nucleic Acids Res* 30:E9.
8. Hamers-Casterman, C., Atarhouch, T., Muyldermans, S., Robinson, G., Hamers, C. Songa, E. B., Bendahman, N., Hamers, R. (1993) *Nature* 363:446-8.
9. Hussack, G., Arbabi-Ghahroudi, M., van Faassen, H., Songer, J. G., Ng, K. K., MacKenzie, R., Tanha, J. (2011a) *J Biol Chem* 286:8961-76. *PLoS One* 6:e28218.
11. Jespers, L., Schon, O., James, L. C., Veprintsev, D., Winter G. (2004) *J Mol Biol* 337:893-903.
12. Kabat, E. A., Wu, T. T., (1991) J Immunol 147:1709-1719.
13. Kim, D. Y., Kandalaft, H., Ding, W., Ryan, S., van Faassen, H., Hirama, T., Foote, S. J., MacKenzie, R., Tanha, J. (2012) *Protein Eng Des Sel* 25:581-9.
14. Li, S., Zheng, W., Kuolee, R., Hirama, T., Henry, M., Makvandi-Nejad, S., Fjällman, T., Chen, W., Zhang, J. (2009) *Mol Immunol* 46:1718-26.
15. Merritt, E. A., Hol, W. G. (1995) *Curr Opin Struct Biol* 5:165-71.
16. Nicaise, M., Valerio-Lepiniec, M., Minard, P., Desmadril, M. (2004) *Protein Sci* 13:1882-91.
17. Nuttall, S. D., Krishnan, U. V., Doughty, L., Pearson, K., Ryan, M. T., Hoogenraad, N. J., Hattarki, M., Carmichael, J. A., Irving, R. A., Hudson, P. J. (2003) *Eur J Biochem* 270:3543-54.
18. Ridgway, J. B., Presta, L. G., Carter, P. (1996) *Protein Eng* 9:617-21.
19. To, R., Hirama, T., Arbabi-Ghahroudi, M., MacKenzie, R., Wang, P., Xu, P., Ni, F., Tanha, J. (2005) *J Biol Chem* 280:41395-403.
20. Zhang, J., Tanha, J., Hirama, T., Khieu, N. H., To, R., Tong-Sevinc, H., Stone, E., Brisson, J. R., MacKenzie, C. R. (2004a)*J Mol Biol* 335:49-56.
21. *J Mol Biol* 341:161-9.
22. Zhu, X., Wang, L., Liu, R., Flutter, B., Li, S., Ding, J., Tao, H., Liu, C., Sun, M., Gao, B. (2010) *Immunol Cell Biol* 88:667-75.
23. Marcos-Silva, L. et al. J. Proteome Res. 2014, 13, 3349-3359.

The invention claimed is:

1. An antibody or an antigen-binding fragment thereof that binds to O-glycan mucin-type glycoprotein MUC16, comprising three variable heavy domain complementarity determining regions (CDR) (CDR H1, H2, and H3), and three variable light domain CDR (CDR L1, L2, and L3), wherein the CDR H1, H2, H3, L1, L2, and L3 comprise the amino acid sequence:

CDR H1:
(SEQ ID NO: 1)
GFTFSTF,

CDR H2:
(SEQ ID NO: 2)
SSGSST,

CDR H3:
(SEQ ID NO: 3)
SGYDYDPIYYALDY,

CDR L1:
(SEQ ID NO: 4)
RASESVDNYGISFMN,

```
CDR L2:
                                    (SEQ ID NO: 5)
GASNQGS,
and

CDR L3:
                                    (SEQ ID NO: 6)
QQTKEVPWT.
```

2. The antibody or the antigen binding fragment thereof of claim 1, further comprising four variable heavy domain framework regions (HFR)(HFR 1, 2, 3, and 4), wherein the HFR 1, 2, 3, and 4 comprise the amino acid sequence:

```
HFR 1:
                                    (SEQ ID NO: 7)
EVQLVESGGGLVQPGGSRKLSCAAS,

HFR 2:
                                    (SEQ ID NO: 8)
GMHWVRQAPEKGLEWVAYI,

HFR 3:
                                    (SEQ ID NO: 9)
IYYGDTLQGRFIISRDNPKNTLFLQMTSLRSEDTAMYYCAR,
and

HFR 4:
                                    (SEQ ID NO: 10)
WGQGTSVTVSS.
```

3. The antibody or the antigen binding fragment thereof of claim 1, further comprising four variable light domain framework regions (LFR) (LFR 1, 2, 3, and 4), wherein the LFR 1, 2, 3, and 4 comprise the amino acid sequence:

```
LFR 1:
                                    (SEQ ID NO: 11)
DIVLTQSPASLAVSLGQRATISC,

LFR 2:
                                    (SEQ ID NO: 12)
WFQQKPGHPPKLLIY,

LFR 3:
                                    (SEQ ID NO: 13)
GVPARFSGSGSGTDFSLNIHPMEEDDAAMYFC,
and

LFR 4:
                                    (SEQ ID NO: 14)
FGGGTKVEIKR.
```

4. The antibody or the antigen binding fragment thereof of claim 1, comprising a variable heavy domain (VH) comprising the amino acid sequence:

```
                                    (SEQ ID NO: 15)
EVQLVESGGGLVQPGGSRKLSCAASGFTFSTFGMHWVRQAPEKGLEWVAY

ISSGSSTIYYGDTLQGRFIISRDNPKNTLFLQMTSLRSEDTAMYYCARSG

YDYDPIYYALDYWGQGTSVTVSS.
```

5. The antibody or the antigen binding fragment thereof of claim 1, comprising a variable light domain (VL) comprising the amino acid sequence:

```
                                    (SEQ ID NO: 16)
DIVLTQSPASLAVSLGQRATISCRASESVDNYGISFMNWFQQKPGHPPKL

LIYGASNQGSGVPARFSGSGSGTDFSLNIHPMEEDDAAMYFCQQTKEVPW

TFGGGTKVEIKR.
```

6. The antibody or the antigen binding fragment thereof of claim 1, comprising a variable heavy domain (VH) comprising the amino acid sequence:

```
                                    (SEQ ID NO: 15)
EVQLVESGGGLVQPGGSRKLSCAASGFTFSTFGMHWVRQAPEKGLEWVAY

ISSGSSTIYYGDTLQGRFIISRDNPKNTLFLQMTSLRSEDTAMYYCARSG

YDYDPIYYALDYWGQGTSVTVSS,
``` and
   a variable light domain (VL) comprising the amino acid sequence:

```
                                    (SEQ ID NO: 16)
DIVLTQSPASLAVSLGQRATISCRASESVDNYGISFMNWFQQKPGHPPKL

LIYGASNQGSGVPARFSGSGSGTDFSLNIHPMEEDDAAMYFCQQTKEVPW

TFGGGTKVEIKR.
```

7. The antibody or the antigen binding fragment thereof of claim 1, wherein the antibody is an IgA, IgD, IgE, IgG, or IgM.

8. The antibody or the antigen binding fragment thereof of claim 1, wherein the antigen-binding fragment is a single domain antibody (sdAb) or a single-chain variable fragment (scFv).

9. The antibody or the antigen binding fragment thereof of claim 1, wherein the antibody or the antigen-binding fragment thereof is humanized or partially humanized.

10. The antibody or the antigen binding fragment thereof of claim 1, wherein the antibody is POCmAb.

11. A composition, comprising the antibody or the antigen binding fragment thereof of claim 1 and a pharmaceutically acceptable diluent, carrier, or excipient.

12. A method of inhibiting tumor growth of a tumor expressing O-glycan mucin-type glycoprotein MUC16 in a subject in need thereof, comprising administering to the subject the antibody or the antigen binding fragment thereof that targets O-glycan mucin-type glycoprotein MUC16 of claim 1.

13. The method of claim 12, wherein the antibody or the antigen binding fragment thereof is an antibody.

14. The method of claim 13, wherein the antibody is a monoclonal antibody.

15. The method of claim 12, further comprising administering a second therapeutic agent comprising at least one of a cytotoxic agent, an additional antibody or a therapeutically active fragment thereof, or a chemotherapy regimen.

16. The method of claims 15, wherein the cytotoxic agent is at least one of an inhibitor of ErbB signaling, an inhibitor of phosphoinositide 3-kinases (PI3Ks)/Akt signaling, gemcitabine and abraxane or combinations thereof;
   wherein the additional antibody or therapeutically fragment thereof is oregovomab antibody B43.13, AR9.6 antibody, or combinations thereof; and
   wherein the chemotherapy regimen is Folfirinox.

17. The method of claim 12, wherein the tumor is chosen from a pancreatic tumor, a gall bladder tumor, a gastric tumor, a colon tumor, an ovarian tumor, a breast tumor, and a liver tumor.

18. The method of claim 12, wherein the method is for the treatment of a cancer.

* * * * *

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: CDR H1

<400> SEQUENCE: 1

Gly Phe Thr Phe Ser Thr Phe
1               5

<210> SEQ ID NO 2
<211> LENGTH: 6
<212> TYPE: PRT
<213> ORGANISM: Artificial Sequence
```

```
<220> FEATURE:
<223> OTHER INFORMATION: CDR H2

<400> SEQUENCE: 2

Ser Ser Gly Ser Ser Thr
1               5

<210> SEQ ID NO 3
<211> LENGTH: 14
<212> TYPE: PRT
<213> ORGANISM: Artificial Sequence
<220> FEATURE:
<223> OTHER INFORMATION: CDR H3

<400> SEQUENCE: 3

Ser Gly Tyr Asp Tyr Asp Pro Ile Tyr Tyr Ala Leu Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDR L1

<400> SEQUENCE: 4

Arg Ala Ser Glu Ser Val Asp Asn Tyr Gly Ile Ser Phe Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR L2

<400> SEQUENCE: 5

Gly Ala Ser Asn Gln Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR L3

<400> SEQUENCE: 6

Gln Gln Thr Lys Glu Val Pro Trp Thr
1               5

<210> SEQ ID NO 7
<211> LENGTH: 25
<212> TYPE: PRT
<213> ORGANISM: Artificial Sequence
<220> FEATURE:
<223> OTHER INFORMATION: HFR 1

<400> SEQUENCE: 7

Glu Val Gln Leu Val Glu Ser Gly Gly Gly Leu Val Gln Pro Gly Gly
1               5                   10                  15

Ser Arg Lys Leu Ser Cys Ala Ala Ser
            20                  25
```

```
<210> SEQ ID NO 8
<211> LENGTH: 19
<212> TYPE: PRT
<213> ORGANISM: Artificial Sequence
<220> FEATURE:
<223> OTHER INFORMATION: HFR 2

<400> SEQUENCE: 8

Gly Met His Trp Val Arg Gln Ala Pro Glu Lys Gly Leu Glu Trp Val
1               5                   10                  15

Ala Tyr Ile

<210> SEQ ID NO 9
<211> LENGTH: 41
<212> TYPE: PRT
<213> ORGANISM: Artificial Sequence
<220> FEATURE:
<223> OTHER INFORMATION: HFR 3

<400> SEQUENCE: 9

Ile Tyr Tyr Gly Asp Thr Leu Gln Gly Arg Phe Ile Ile Ser Arg Asp
1               5                   10                  15

Asn Pro Lys Asn Thr Leu Phe Leu Gln Met Thr Ser Leu Arg Ser Glu
            20                  25                  30

Asp Thr Ala Met Tyr Tyr Cys Ala Arg
        35                  40

<210> SEQ ID NO 10
<211> LENGTH: 11
<212> TYPE: PRT
<213> ORGANISM: Artificial Sequence
<220> FEATURE:
<223> OTHER INFORMATION: HFR 4

<400> SEQUENCE: 10

Trp Gly Gln Gly Thr Ser Val Thr Val Ser Ser
1               5                   10

<210> SEQ ID NO 11
<211> LENGTH: 23
<212> TYPE: PRT
<213> ORGANISM: Artificial Sequence
<220> FEATURE:
<223> OTHER INFORMATION: LFR 1

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: LFR 2

<400> SEQUENCE: 12

Trp Phe Gln Gln Lys Pro Gly His Pro Pro Lys Leu Leu Ile Tyr
1               5                   10                  15
```

```
<210> SEQ ID NO 13
<211> LENGTH: 32
<212> TYPE: PRT
<213> ORGANISM: Artificial Sequence
<220> FEATURE:
<223> OTHER INFORMATION: LFR 3

<400> SEQUENCE: 13

Gly Val Pro Ala Arg Phe Ser Gly Ser Gly Ser Gly Thr Asp Phe Ser
1               5                   10                  15

Leu Asn Ile His Pro Met Glu Glu Asp Asp Ala Ala Met Tyr Phe Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: LFR 4

<400> SEQUENCE: 14

Phe Gly Gly Gly Thr Lys Val Glu Ile Lys Arg
1               5                   10

<210> SEQ ID NO 15
<211> LENGTH: 123
<212> TYPE: PRT
<213> ORGANISM: Artificial Sequence
<220> FEATURE:
<223> OTHER INFORMATION: Variable heavy domain

<400> SEQUENCE: 15

Glu Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Leu
    50                  55                  60

Gln Gly Arg Phe Ile Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Tyr Asp Tyr Asp Pro Ile Tyr Tyr Ala Leu Asp Tyr
            100                 105                 110

Trp Gly Gln Gly Thr Ser Val Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: Variable light domain

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30
```

```
Gly Ile Ser Phe Met Asn Trp Phe Gln Gln Lys Pro Gly His Pro Pro
            35                  40                  45

Lys Leu Leu Ile Tyr Gly Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Ala Ala Met Tyr Phe Cys Gln Gln Thr Lys
                 85                  90                  95

Glu Val Pro Trp Thr Phe Gly Gly Gly Thr Lys Val Glu Ile Lys Arg
            100                 105                 110

<210> SEQ ID NO 17
<211> LENGTH: 194
<212> TYPE: PRT
<213> ORGANISM: Artificial Sequence
<220> FEATURE:
<223> OTHER INFORMATION: MUC16 1.2TR

<400> SEQUENCE: 17

Ile Pro Val Pro Thr Ser Ser Thr Pro Gly Thr Ser Thr Val Asp Leu
 1               5                  10                  15

Gly Ser Gly Thr Pro Ser Ser Leu Pro Ser Pro Thr Thr Ala Gly Pro
             20                  25                  30

Leu Leu Val Pro Phe Thr Leu Asn Phe Thr Ile Thr Asn Leu Lys Tyr
            35                  40                  45

Glu Glu Asp Met His Cys Pro Gly Ser Arg Lys Phe Asn Thr Thr Glu
 50                  55                  60

Arg Val Leu Gln Ser Leu Leu Gly Pro Met Phe Lys Asn Thr Ser Val
 65                  70                  75                  80

Gly Pro Leu Tyr Ser Gly Cys Arg Leu Thr Leu Leu Arg Ser Glu Lys
                 85                  90                  95

Asp Gly Ala Ala Thr Gly Val Asp Ala Ile Cys Thr His Arg Leu Asp
            100                 105                 110

Pro Lys Ser Pro Gly Val Asp Arg Glu Gln Leu Tyr Trp Glu Leu Ser
            115                 120                 125

Gln Leu Thr Asn Gly Ile Lys Glu Leu Gly Pro Tyr Thr Leu Asp Arg
 130                 135                 140

Asn Ser Leu Tyr Val Asn Gly Phe Thr His Gln Thr Ser Ala Pro Asn
145                 150                 155                 160

Thr Ser Thr Pro Gly Thr Ser Thr Val Asp Leu Gly Thr Ser Gly Thr
                165                 170                 175

Pro Ser Ser Leu Pro Ser Pro Thr Ser Ala Gly Pro Leu Leu Val Pro
            180                 185                 190

Phe Thr
```